(12) United States Patent
Smith et al.

(10) Patent No.: US 12,085,559 B2
(45) Date of Patent: Sep. 10, 2024

(54) REPLACEABLE GROUND ELECTRODE FOR ELECTROPHYSIOLOGY, ELECTRODE REJUVENATING APPARATUS, AND RELATED METHODS AND SYSTEMS

(71) Applicant: Molecular Devices, LLC, San Jose, CA (US)

(72) Inventors: Thomas L. Smith, Campbell, CA (US); Edward Verdonk, San Jose, CA (US)

(73) Assignee: Molecular Devices, LLC, San Jose, CA (US)

( * ) Notice: Subject to any disclaimer, the term of this patent is extended or adjusted under 35 U.S.C. 154(b) by 0 days.

(21) Appl. No.: 17/361,860

(22) Filed: Jun. 29, 2021

(65) Prior Publication Data

US 2021/0325366 A1   Oct. 21, 2021

Related U.S. Application Data

(62) Division of application No. 15/112,504, filed as application No. PCT/US2015/012053 on Jan. 20, 2015, now Pat. No. 11,067,563.

(60) Provisional application No. 61/930,330, filed on Jan. 22, 2014.

(51) Int. Cl.
*G01N 33/487* (2006.01)
*G01N 27/38* (2006.01)

(52) U.S. Cl.
CPC ....... *G01N 33/48728* (2013.01); *G01N 27/38* (2013.01)

(58) Field of Classification Search
CPC .......................... G01N 33/48728; G01N 27/38
See application file for complete search history.

(56) References Cited

U.S. PATENT DOCUMENTS

| 4,466,878 A | 8/1984 | DiNitto |
| 4,549,951 A | 10/1985 | Knudson |
| 4,818,361 A | 4/1989 | Burgess |
| 4,871,439 A | 10/1989 | Enzer |
| 4,902,399 A | 2/1990 | Durley, III |

(Continued)

FOREIGN PATENT DOCUMENTS

| CN | 102224415 | 10/2011 |
| CN | 102884427 | 1/2013 |

(Continued)

OTHER PUBLICATIONS

Chinese 1st Office Action and Search Report in Application 201580015018.1, mailed Jun. 23, 2017, 6 pages.

(Continued)

*Primary Examiner* — Luan V Van
*Assistant Examiner* — Shizhi Qian
(74) *Attorney, Agent, or Firm* — Merchant & Gould P.C.

(57) ABSTRACT

A plenum assembly configured for electrophysiology assays, such as patch clamp techniques, includes one or more ground electrode assemblies. The ground electrode assemblies are individually removable from a plenum base of the plenum assembly in a non-destructive manner, and may be reinstalled in the plenum base in a manner that reestablishes electrical contact with ground circuitry without requiring soldering or other additional steps. A rejuvenating apparatus is provided for rejuvenating one or more ground electrode assemblies removed from the plenum base.

5 Claims, 14 Drawing Sheets

(56) References Cited

U.S. PATENT DOCUMENTS

| | | |
|---|---|---|
| 6,488,829 B1 | 12/2002 | Schroeder et al. |
| 7,429,316 B1 | 9/2008 | Osipchuk |
| 8,048,289 B2 | 11/2011 | Finkel |
| 8,323,955 B1 | 12/2012 | Okandan |
| 11,067,563 B2 | 7/2021 | Smith |
| 2002/0064841 A1 | 5/2002 | Klemic et al. |
| 2003/0070923 A1 | 4/2003 | Schroeder et al. |
| 2003/0089623 A1* | 5/2003 | Peat ............... G01N 27/38 204/422 |
| 2006/0141787 A1* | 6/2006 | Ren ............... B08B 3/08 438/689 |
| 2006/0194255 A1 | 8/2006 | Finkel |
| 2007/0137573 A1 | 6/2007 | Kholodenko et al. |
| 2008/0017523 A1* | 1/2008 | Dietze ............... G01N 27/38 204/402 |
| 2008/0236620 A1* | 10/2008 | Shih ............... B08B 3/12 134/28 |
| 2011/0251102 A1* | 10/2011 | Osipchuk ......... G01N 33/48728 506/10 |
| 2013/0048511 A1 | 2/2013 | Verdonk |
| 2013/0060478 A1 | 3/2013 | Osipchuk |
| 2017/0089882 A1 | 3/2017 | Smith |

FOREIGN PATENT DOCUMENTS

| | | |
|---|---|---|
| CN | 103477223 | 12/2013 |
| EP | 1475820 | 11/2004 |
| GB | 2122354 | 6/1982 |
| GB | 2231656 | 11/1990 |
| GB | 2401689 | 11/2004 |
| JP | 2010-008399 | 1/2010 |
| JP | 2010510419 | 4/2010 |
| JP | 2013-523150 | 6/2013 |
| JP | 2014-525582 | 9/2017 |
| WO | 2013/033225 | 3/2013 |
| WO | 2013/094418 | 6/2013 |

OTHER PUBLICATIONS

Chinese 3rd Office Action and Supplementary Search Report in Application 201580015018.1, mailed Aug. 27, 2018, 8 pages.

European Extended Search Report in Application 20183201.1, mailed Oct. 22, 2020, 6 pages.

European Search Report in Application 15740076.3, mailed Jul. 17, 2020, 9 pages.

Japanese Notice of Allowance in Application2016547888, mailed May 28, 2019, 5 pages.

Japanese Refusal and Search Report in Application2016547888, mailed Jul. 11, 2018, 18 pages.

Japanese Notice of Reasons for Refusal in Application 2019-118139, mailed Aug. 3, 2020, 2 pages.

Ogden, D., "Patch clamp techniques for single channel and whole cell recording", Microelectrode Techniques, Dec. 31, 1994, pp. 53-128.

PCT International Preliminary Report on Patentability in PCT/US2015/012053 mailed Aug. 4, 2016, 9 pages.

PCT International Search Report and Written Opinion for PCT/US2015/012053 dated Apr. 27, 2015, 11 pages.

* cited by examiner

REPLACEABLE GROUND ELECTRODE FOR ELECTROPHYSIOLOGY, ELECTRODE REJUVENATING APPARATUS, AND RELATED METHODS AND SYSTEMS

RELATED APPLICATION

This application is a divisional application of U.S. patent application Ser. No. 15/112,504, now U.S. Pat. No. 11,067, 563, filed Jul. 19, 2016, which application is a National Stage Application of PCT/US2015/012053, filed Jan. 20, 2015, which claims the benefit of U.S. Patent Application Ser. No. 61/930,330, filed Jan. 22, 2014, the disclosures of which are incorporated by reference herein in their entirety.

TECHNICAL FIELD

The present invention relates to electrophysiology and apparatuses and methods for carrying out electrophysiological measurements and assays. More specifically, the invention relates to ground electrodes utilized in such apparatuses and methods, and to apparatuses and methods for rejuvenating ground electrodes.

BACKGROUND

Electrophysiology entails the study of the electrical behavior of biological cells and cell membranes, such as transmembrane potentials and the flow of transmembrane current through membrane-associated ion channels. Patch clamp techniques are widely utilized for performing electrophysiological measurements. Various patch clamp techniques are known to persons skilled in the art. In one type of planar patch clamp technique, cell suspensions are pipetted into the wells of a microplate. The microplate is mounted onto a plenum containing an ionic solution. The bottom of each well has at least one micro-scale aperture communicating with the plenum interior. Ground electrodes are permanently mounted at the bottom of the plenum interior, i.e., at the base of a plenum assembly. Sense electrodes communicating with measurement electronics are inserted into the respective wells. A slight vacuum is applied to the plenum interior to pull cells toward the well apertures. The vacuum causes a cell to form a high-resistance electrical seal with the boundary of a given aperture, thus completing an electrical circuit that includes the cell sealed at the aperture. Assays are then carried out and electrophysiological measurement data acquired according to methods appreciated by persons skilled in the art.

The ground electrodes are slightly porous and thus allow fluid to permeate them. With repeated use and over time, the ground electrodes deteriorate due to the electrochemical activity associated with the conversion of electrical current into ionic current in solution. Specifically, the products of the electrochemical activity (contaminants, or toxins) build up in the bulk of the ground electrodes. This build up eventually impairs the assays being performed, necessitating replacement or at least rejuvenation (reconditioning, cleaning, etc.) of the ground electrodes. Typically, the electrophysiological measurement apparatus is operated throughout the day to maximize assay throughput. Hence, ground electrodes may deteriorate on a daily basis as a result of such frequent use.

In conventional plenum configurations, the ground electrodes are permanently mounted to the plenum base as noted above. Consequently, rejuvenating or replacing any one ground electrode requires a technician to remove the entire plenum assembly (including the base, which contains all of the ground electrodes) from the apparatus for rejuvenation or disposal. To be able to continue operating the apparatus, the technician must then install another plenum assembly. The requirement to replace entire plenum assemblies on a daily basis is neither practical nor convenient, and involves a significant amount of skill as well as operational downtime. Moreover, rejuvenation typically entails soaking the plenum base in a bath of a rejuvenating fluid such as a salt solution. In conventional plenum configurations, only the top surfaces of the ground electrodes are exposed to the ambient. The sides and bottom surfaces of the ground electrodes are hermetically sealed with epoxy or other type of potting material and thus cannot be accessed by the rejuvenating fluid except by diffusion. Consequently, in the conventional rejuvenation process the rejuvenating fluid passively diffuses into a ground electrode from only one side, i.e., its top surface. As a result, the conventional rejuvenation process can require a significant amount of time, for example twelve hours. Furthermore, in conventional plenum configurations a ground wire is permanently connected to the bottom surface of each ground electrode and is soldered to circuitry below the ground electrode. Once the plenum assembly is removed from the associated electrophysiological measurement apparatus, removal of the plenum base (housing the ground electrodes) from the plenum assembly requires breaking the solder joint, and disassembling the plenum assembly (e.g., plenum base, manifold, sealing components, etc.). Hence, subsequent reinstallation of the plenum base or replacement with a new plenum base requires (re-)soldering the ground wire to the circuitry and reassembling the plenum assembly, thereby adding to the skill and downtime involved. Additionally, the handling and transport of the plenum base must be done carefully to avoid damaging the ground wires and breaking or compromising their electrical connections to the corresponding ground electrodes.

In view of the foregoing, there is a need for providing ground electrode and plenum configurations that improve the ability to remove and replace ground electrodes, and to reestablish electrical connections upon replacement. There is also a need for providing improved apparatuses and methods for rejuvenating ground electrodes.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a ground electrode assembly for electrophysiology includes: a housing comprising a top housing surface, a bottom housing surface, an inside housing surface, a first chamber open at the top housing surface, and a second chamber open at the bottom housing surface, wherein the inside housing surface comprises an inside shoulder defining an inside opening and the second chamber communicates with the first chamber at the inside opening; and an electrode comprising a top electrode surface, a bottom electrode surface, and an outside lateral electrode surface, the electrode positioned in the first chamber such that the outside lateral electrode surface faces the inside housing surface at an interface, and a portion of the bottom electrode surface is exposed to the second chamber at the inside opening.

According to another embodiment, the housing includes a receptacle for receiving a tool, the receptacle extending into the housing from the top housing surface.

According to another embodiment, the sealing member is located at a corner at which the first inside lateral housing surface adjoins the shoulder.

According to another embodiment, the shoulder includes a transverse section transverse to the axis and a channel between the transverse section and the first inside lateral housing surface, and the sealing member is located in the channel.

According to another embodiment, the sealing member has a composition suitable for adhering the electrode to the housing in a permanent manner.

According to another embodiment, the ground electrode assembly includes a ground circuit in signal communication with the bottom electrode surface.

According to another embodiment, at least a portion of the ground circuit is mounted at the plenum base.

According to another embodiment, at least a portion of the ground circuit is located in the second chamber.

According to another embodiment, the ground circuit includes a spring, and the spring is mounted in the mounting receptacle such that the spring is compressed into contact with the bottom electrode surface when the ground electrode assembly is mounted in the mounting receptacle.

According to another embodiment, the housing includes an external thread, and the plenum base includes an internal thread configured to engage the external thread such that the ground electrode assembly is removably mounted in the mounting receptacle by threading the ground electrode assembly into the mounting receptacle, and wherein the spring includes a helical winding that turns in an opposite handedness than the internal thread and the external thread.

According to another embodiment, the ground circuit includes a plug extending into the second chamber, and the spring is compressed between the bottom electrode surface and the plug when the ground electrode assembly is mounted in the mounting receptacle.

According to another embodiment, the plug comprises a recess in which the spring is positioned.

According to another embodiment, the plug is spaced from the second lateral inside housing surface by a gap, and further including a sealing member located in the gap and configured for fluidly isolating a portion of the second chamber between the bottom electrode surface and the plug from the mounting receptacle.

According to another embodiment, the inside receptacle surface includes a receptacle shoulder, the housing includes a flange section surrounding at least a portion of the electrode, and the flange section contacts the receptacle shoulder when the ground electrode assembly is mounted in the mounting receptacle.

According to another embodiment, the flange section includes an outer lateral flange surface facing the inside receptacle surface at an interface, and further including a sealing member located between the interface and the mounting receptacle for fluidly isolating the interface from the mounting receptacle.

According to another embodiment, the top housing surface is substantially flush with the top base surface.

According to another embodiment, the ground electrode assembly includes a plurality of mounting receptacles open to the top base surface, and a plurality of ground electrode assemblies removably mounted in the mounting receptacles.

According to another embodiment, a ground electrode assembly for electrophysiology includes: a housing having a length along an axis, the housing comprising a top housing surface transverse to the axis, a bottom housing surface transverse to the axis, a first inside lateral housing surface surrounding the axis and having a first transverse dimension, a second inside lateral housing surface surrounding the axis and having a second transverse dimension less than the first transverse dimension, and a shoulder surrounding the axis and defining an inside opening, wherein the first inside lateral housing surface and the shoulder define a first chamber open to the top housing surface, and the second inside lateral housing surface defines a second chamber open to the bottom housing surface, and the second chamber communicates with the first chamber at the inside opening; an electrode comprising a top electrode surface, a bottom electrode surface, and an outside lateral electrode surface, the electrode positioned in the first chamber such that the outside lateral electrode surface faces the first inside lateral housing surface at an interface, and a portion of the bottom electrode surface is exposed to the second chamber at the inside opening; and a sealing member surrounding the axis and located for fluidly isolating the interface from the second chamber.

According to another embodiment, a plenum assembly or plenum base assembly for electrophysiology includes: a ground electrode assembly; and a plenum base comprising a top base surface, a bottom base surface, and an inside receptacle surface defining a mounting receptacle open to the top base surface, wherein the ground electrode assembly is removably mounted in the mounting receptacle.

According to another embodiment, a method for rejuvenating a ground electrode assembly includes: removing the ground electrode assembly from a mounted position in a plenum base, wherein the ground electrode assembly comprises a housing and an electrode positioned in the housing, and at the mounted position the ground electrode assembly is in a mounting receptacle of the plenum base and the electrode is in electrical contact with a ground circuit in the mounting receptacle, and wherein removing the ground electrode assembly comprises moving the electrode out of electrical contact with the ground circuit in a non-destructive manner; and immersing the ground electrode assembly in a rejuvenating fluid for a period of time.

According to another embodiment, removing the ground electrode assembly includes disengaging a first engaging device of the housing from a second engaging device of the plenum base.

According to another embodiment, removing the ground electrode assembly includes threading the ground electrode assembly out from the mounting receptacle.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
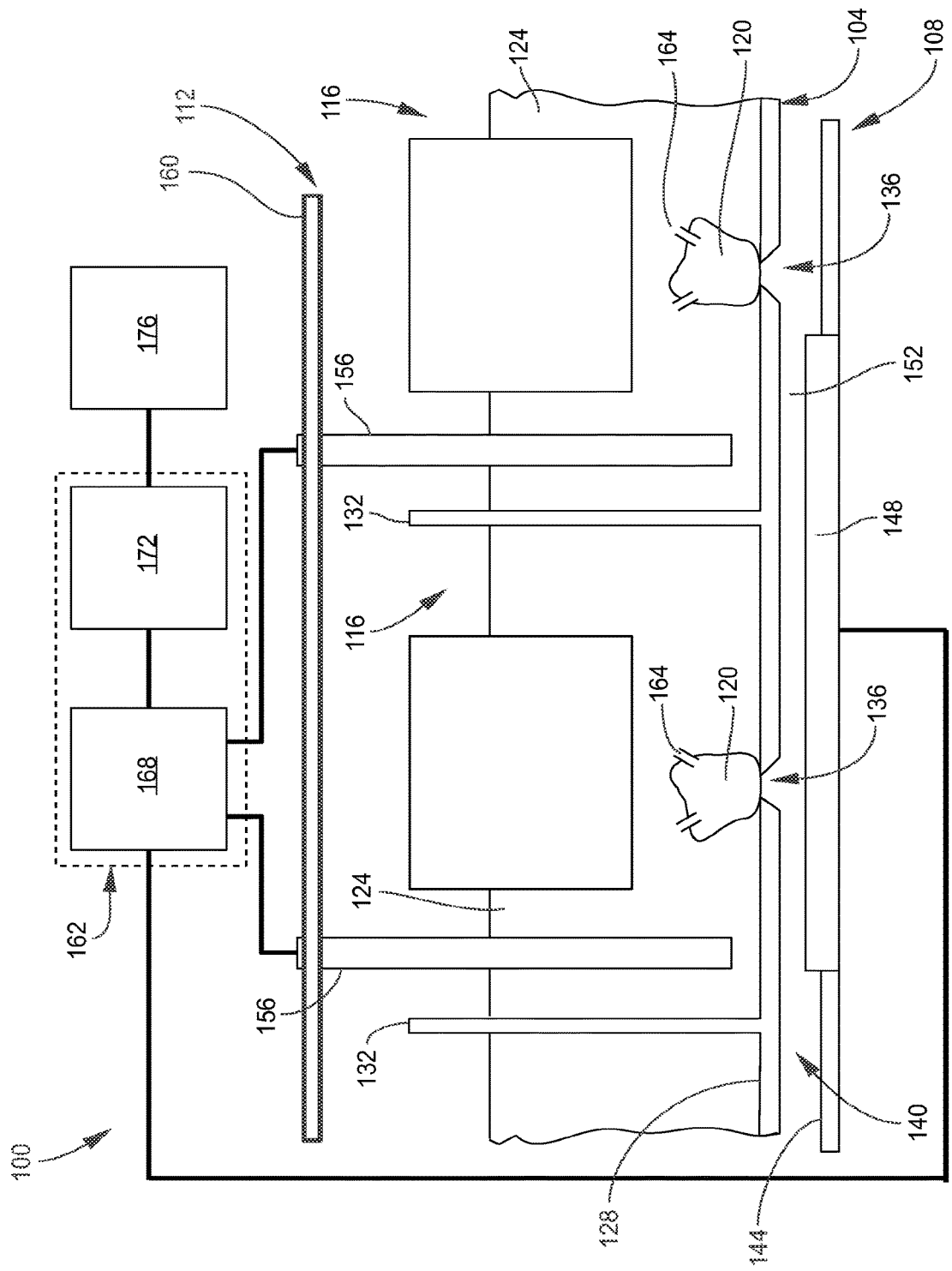
FIG. 1 is a cross-sectional schematic view of an example of an electrophysiology measurement apparatus (or a portion thereof) according to some embodiments.

FIG. 1 is a cross-sectional schematic view of an example of an electrophysiology measurement apparatus 100 (or a portion thereof) according to some embodiments. The apparatus 100 is generally configured for performing electrophysiology measurements, such as in conjunction with patch clamp assays as appreciated by persons skilled in the art. In the illustrated embodiment, the apparatus 100 includes a patch plate 104 interposed between a plenum assembly 108 and an electrode plate 112.

The patch plate 104 may include one or more wells 116 (typically a two-dimensional array of wells 116) for containing biological samples (e.g., cells 120) to be analyzed, external buffer solution 124, and biological screening compounds. For example, the patch plate 104 may be configured in a standard format such as an SBS-standard (Society for Biomolecular Sciences) 384-well microplate format. FIG. 1 illustrates two adjacent wells 116 by way of example. The wells 116 may be bounded by a common bottom wall 128 and partitioned from each other by upright walls 132. Each well 116 communicates with one or more apertures 136 formed through the bottom wall 128. A patch plate 104 having one aperture 136 per well may be referred to as a single-hole plate, while a patch plate having multiple apertures 136 per well 116 may be referred to as a population patch clamp (PPC) plate. Each aperture 136 may have a diameter of, for example, about 1 μm to 2 μm.

The plenum assembly 108 includes a plenum reservoir 140 and a plenum base 144 serving as the lower boundary of the plenum reservoir 140. The plenum base 144 includes one or more ground electrodes 148 exposed to the plenum reservoir 140. The patch plate 104 is mounted onto the plenum assembly 108 such that the bottom wall 128 of the patch plate 104 serves as the upper boundary of the plenum reservoir 140. The plenum assembly 108 includes a sealing member such as an O-ring (not shown) positioned around its perimeter to create an air-tight seal between the patch plate 104 and the plenum reservoir 140 when the patch plate 104 is installed on the plenum assembly 108. In operation during an assay, the plenum reservoir 140 is filled with an internal buffer solution 152 (such as by utilizing a pump and fluidic circuit), which typically is a salt solution (e.g., potassium chloride at relatively high concentration) that emulates the internal cytoplasm of a biological cell. The external buffer solution 124 carrying biological cells to be analyzed is dispensed into the wells 116 of the patch plate 104. The external buffer solution 124 is typically a salt solution (e.g., sodium chloride at relatively high concentration) that emulates extracellular fluid. A small negative pressure (vacuum) is applied to the plenum reservoir 140 to pull cells to the aperture(s) 136 of each well 116, thereby forming high-resistance electrical seals (typically 50-100 megaohm seals) between the cell membranes and the bottom wall 128 at the corresponding apertures 136.

The electrode plate 112 includes one or more sense electrodes 156 typically a two-dimensional array of sense electrodes 156) supported in a frame 160. The sense electrodes 156 typically have an elongated geometry (e.g., pin-shaped), and often are silver wires coated with silver chloride. Typically, one sense electrode 156 is provided for each well 116 of the patch plate 104. For example, the electrode plate 112 may include 384 sense electrodes 156. The electrode plate 112 is mounted onto the patch plate 104 such that a sense electrode 156 extends into each well 116 and is immersed in the external buffer solution 124. Thus, the sense electrodes 156 and the ground electrodes 148 are located on opposite sides of the well apertures 136 (and thus on opposite sides of the sealed cells 120). The sense electrodes 156 and the ground electrodes 148 are in signal communication with measurement electronics 162. With the external buffer solution 124 added to the wells 116 and the internal buffer solution 152 added to the plenum reservoir 140, an electrical circuit is completed across the sealed cell 120 in each well 116 enabling electrophysiological measurements to be performed on each sealed cell 120, such as the electrical activity of ion channels 164. The number of electrical channels of the overall electrical circuit corresponds to the number of sense electrodes 156 utilized.

In some embodiments, the measurement electronics 162 may include a programmable voltage source (not shown) for applying voltages to the sense electrodes 156, an amplifier 168 for converting current measured on the sense electrodes 156 to an analog voltage signals, and an analog-to-digital converter (ADC) 172 for converting analog voltage signals from the amplifier 168 into digital voltage signals. The measurement electronics 162 may communicate with a data acquisition engine 176. The data acquisition engine 176 may be configured for performing any further signal processing needed, storing the digital voltage measurements from the sense electrode channels in a computer memory, outputting data for readout/display, etc.

In some embodiments, an electrophysiology measurement apparatus such as described above may be utilized in an automated, high-throughput electrophysiology measurement system, as appreciated by persons skilled in the art. The system may provide a platform at which a variety of different functional stations or modules are located. Such stations may include, for example, an analysis station at which the components of the electrophysiology measurement apparatus 100 operates; a tip rack station holding pipettor tips utilized to dispense and aspirate buffer solutions, compounds, and biological cells at appropriate times during a given assay; buffer stations for supplying internal and external buffer solutions; compound stations for supplying biological screening compounds, reagents, etc.; a wash station for washing/rinsing various components of the system; a cell station for supplying cells for analysis; etc. The system may also include a robotic pipettor head to which pipettor tips are removably mounted. The robotic pipettor head may be coupled to a fluidics system and to a two- or three-dimensional gantry. The robotic pipettor head is movable to various stations on the system platform (such as the patch plate 104) to dispense and/or aspirate fluids in accordance with the protocol of a given assay. The robotic pipettor head may be configured for gripping the electrode plate 112, transporting the electrode plate 112 to the analysis station, and lowering the electrode plate 112 onto the patch plate 104.

The electrophysiology measurement system may also include a control module that controls various operations of the system during an assay. The control module may include, for example, an external microcomputer, display device, and software user interface. The control module may also include a microcontroller interfaced to the external microcomputer for controlling the real-time functional aspects of the system including motion control, fluidics control, and electrical data recording. Accordingly, in some embodiments the measurement electronics 162 and data acquisition engine 176 described above may be considered as being part of or operatively associated with the control module.

Figure 2A:
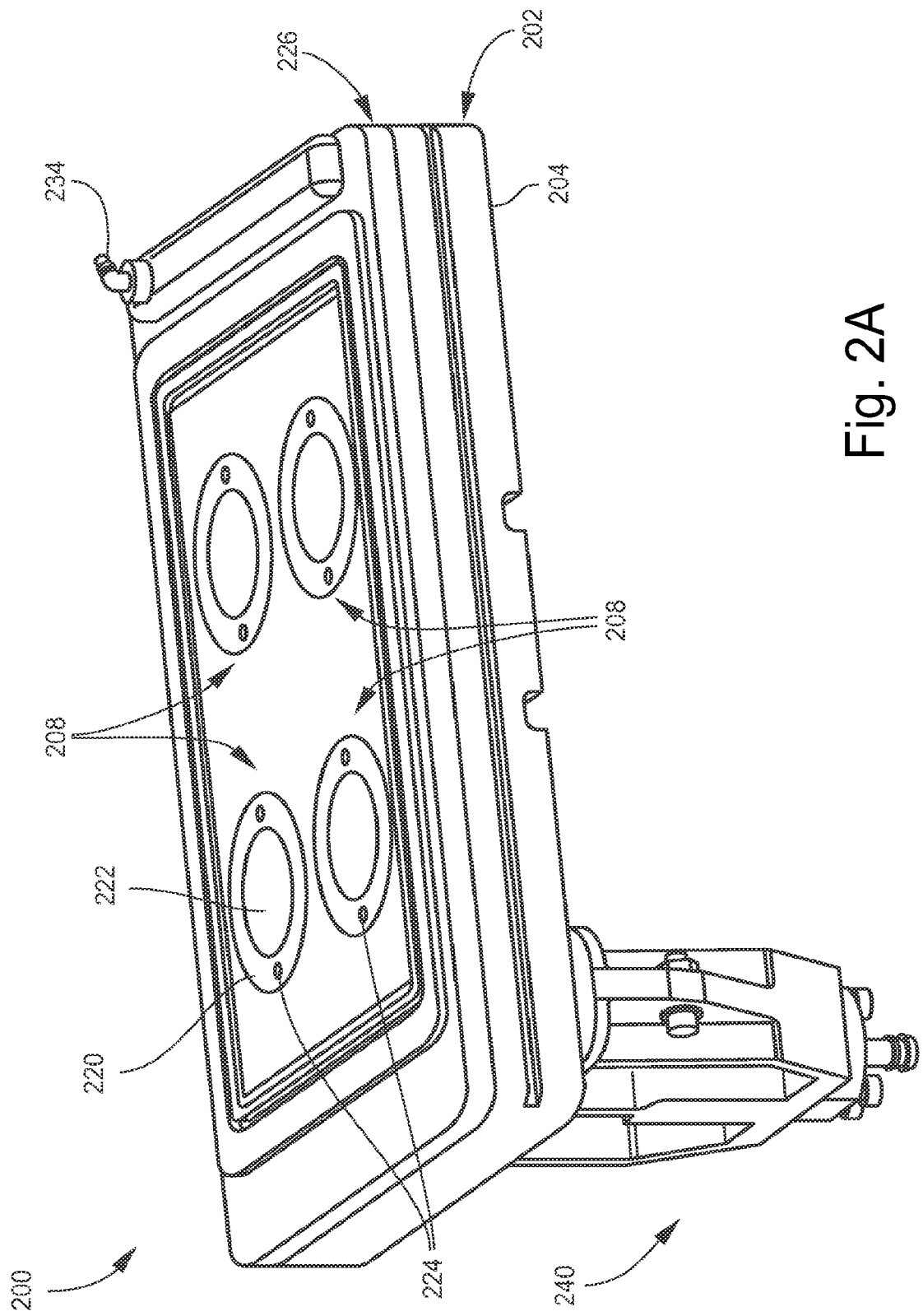
FIG. 2A is a perspective view of a plenum assembly in assembled form according to some embodiments.
Figure 2B:
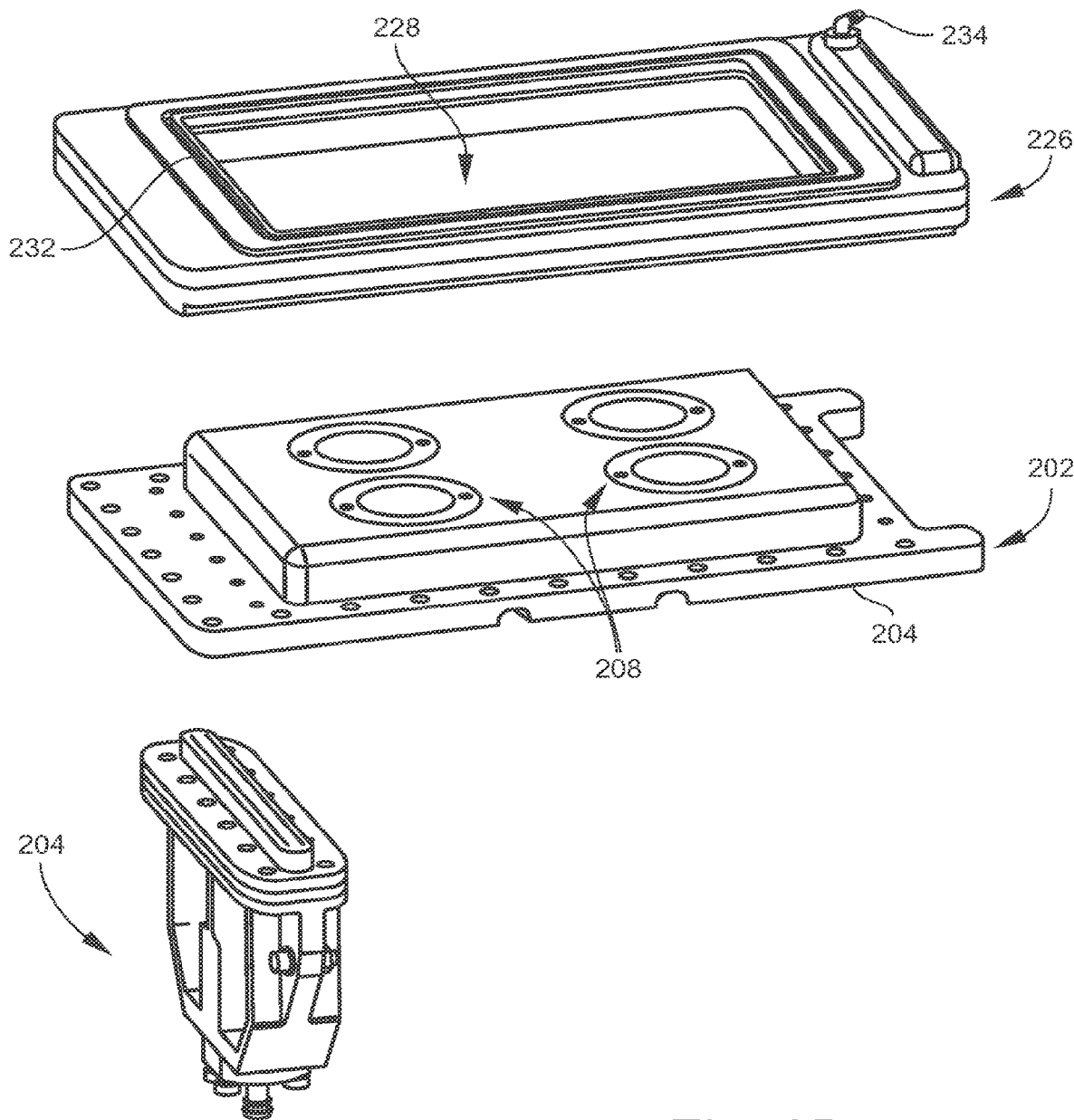
FIG. 2B is a perspective exploded view of the plenum assembly in disassembled form.

FIG. 2A is a perspective view of a plenum assembly 200 in assembled form according to some embodiments. FIG. 2B is a perspective exploded view of the plenum assembly 200 in disassembled form. The plenum assembly 200 may include a plenum base assembly 202, which may include a plenum base 204 and one or more ground electrode assemblies 208. Each ground electrode assembly 208 includes at least one electrode housing 220 and a ground electrode 222 secured in the electrode housing 220. In some embodiments, the ground electrode assembly 208 includes a tool engagement component such as, for example, one or more tool receptacles 224, configured for engaging a tool utilized for aiding in installing and uninstalling the ground electrode assembly 208. When the patch plate 104 is mounted to the plenum assembly 200, the ground electrodes 222 are exposed to the plenum reservoir 140 as shown in FIG. 1. As described further below, the ground electrode assemblies 208 are individually removable from, and re-installable at, the plenum base 204. Thus, the ground electrode assemblies 208 also are individually replaceable as needed. The plenum assembly 200 may also include a top ring assembly 226. The top ring assembly 226 includes an opening 228 into which, in assembled form, a raised portion of the plenum base 204 housing the ground electrode assemblies 208 fits. The top ring assembly 226 also includes a groove or channel 232 surrounding the opening 228. A fluidic sealing component (e.g., O-ring or gasket, not shown) may be seated in the groove or channel 232 to form a vacuum seal surrounding the plenum reservoir 140 when the patch plate 104 is mounted to the plenum assembly 200. The top ring assembly 226 also includes a fitting 234 for connection with a vacuum line. The plenum assembly 200 may also include a manifold assembly 240. The manifold assembly 240 may be configured, and coupled to the plenum base 204, so as allow for a uniform fluid flow pattern across the width of the plenum during plenum fills.

Figure 3A:
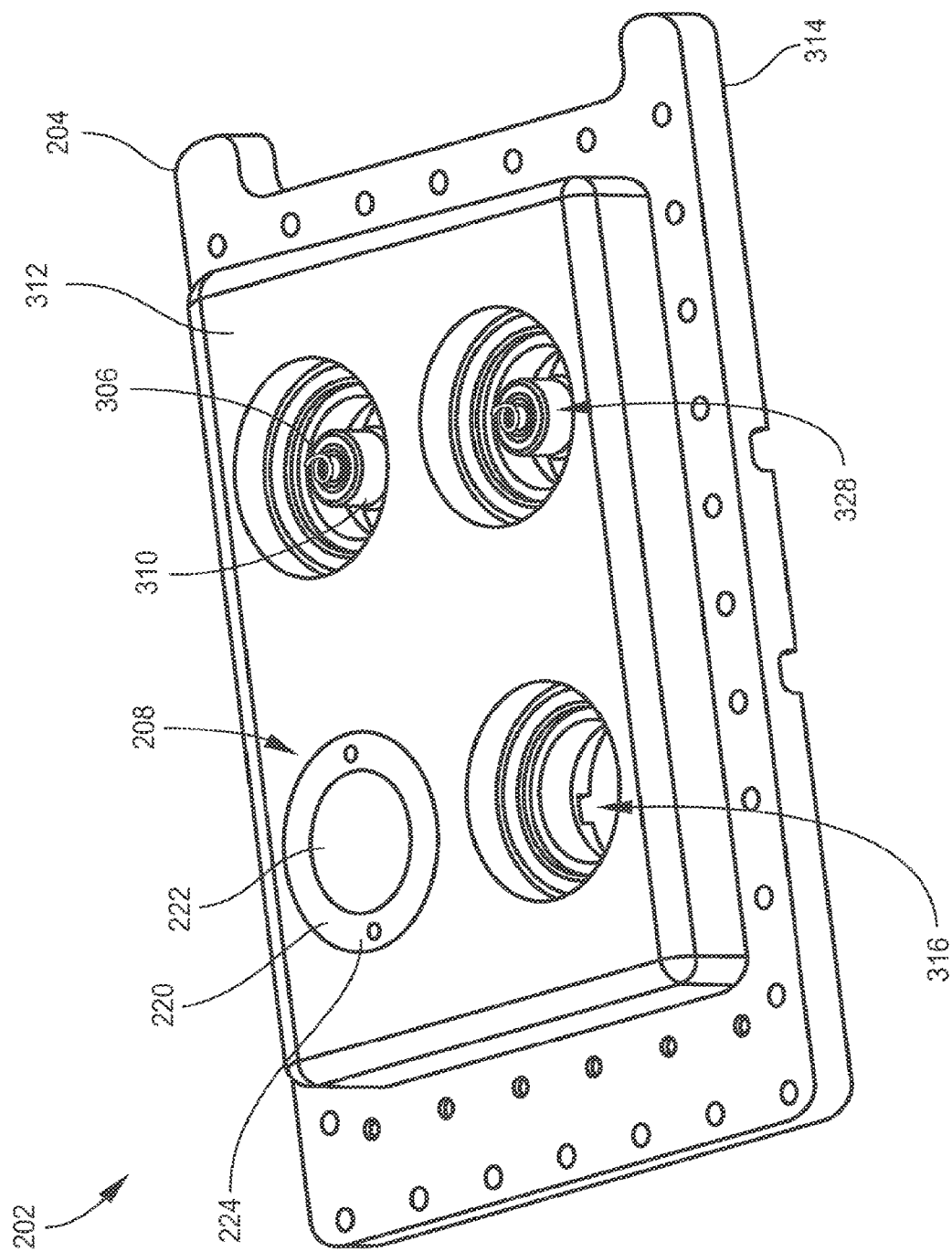
FIG. 3A is a top perspective view of a plenum base assembly of the plenum assembly according to some embodiments.
Figure 3B:
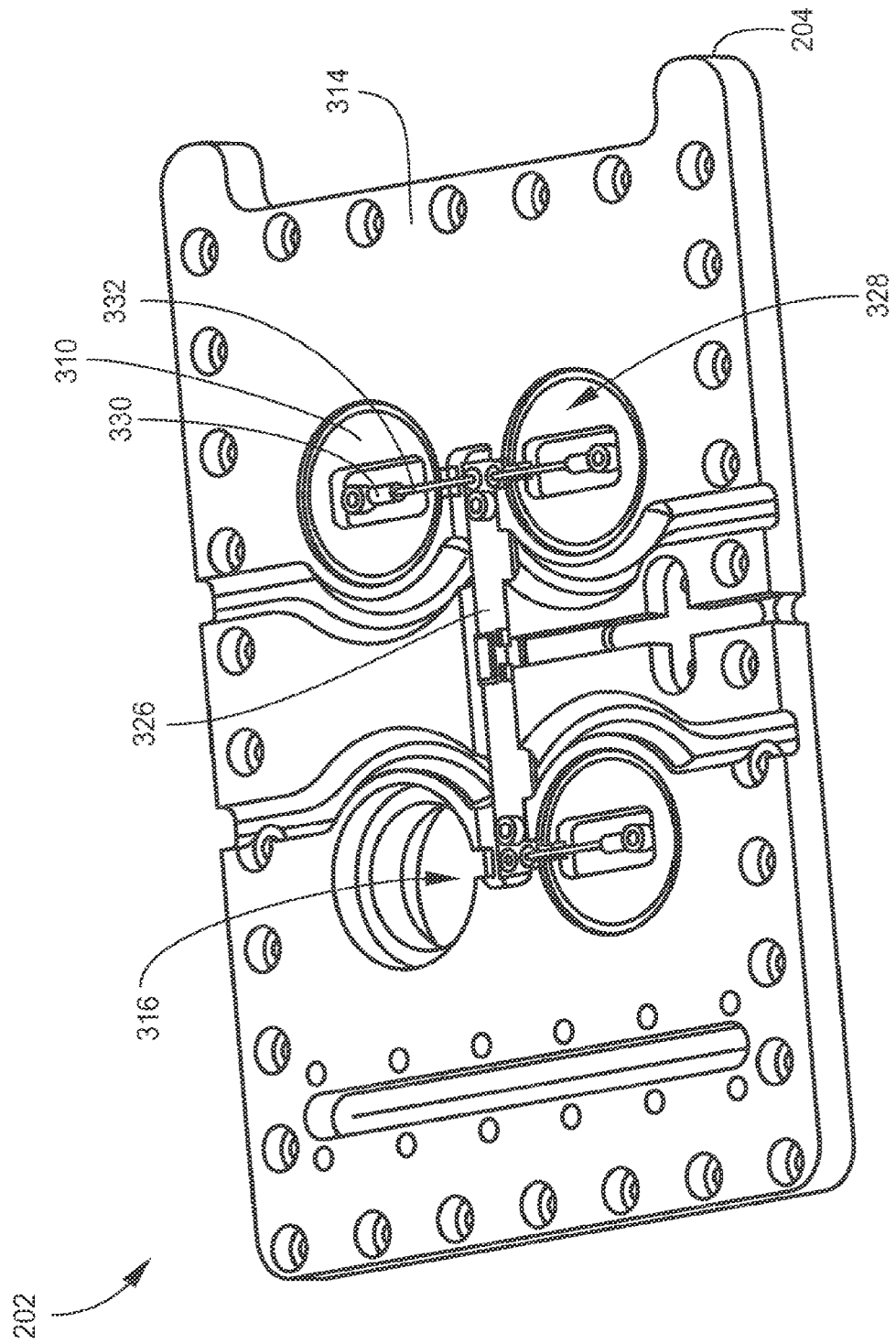
FIG. 3B is a bottom perspective view of the plenum base assembly.

FIG. 3A is a top perspective view of the plenum base assembly 202 according to some embodiments. FIG. 3B is a bottom perspective view of the plenum base assembly 202. The plenum base 204 provides a lower boundary for the plenum reservoir 140 (not shown) that in use contains an internal buffer solution as described above. The plenum base 204 may generally include a top base surface 312, an opposing bottom base surface 314, and one or more mounting receptacles 316 configured for removably mounting one or more corresponding ground electrode assemblies 208. By example only, FIGS. 3A and 3B illustrate four mounting receptacles 316, and only one electrode assembly 208 installed, for purposes of simplifying the illustration. It will be appreciated, however, that more or less mounting receptacles 316 and corresponding ground electrode assemblies 208 may be provided. Each ground electrode assembly 208 is configured for being moved (manipulated) between an installed position in a selected mounting receptacle 316 (FIG. 3A) and an uninstalled position.

The plenum base assembly 202 also includes ground circuit assemblies 328 (ground circuitry or hardware) associated with each mounting receptacle 316 and ground electrode assembly 208 mounted therein. FIGS. 3A and 3B illustrate only three sets of ground circuit assemblies 328 for purposes of simplifying the illustration. Each ground circuit assembly 328 provides signal communication between the corresponding ground electrode 222 and additional circuitry, such as the measurement electronics 162 described above in conjunction with FIG. 1. In the present embodiment, at least a portion of the hardware 328 is located in the mounting receptacle 316. When the ground electrode assembly 208 is in the installed position, a bottom electrode surface of the ground electrode 222 faces the interior of the mounting receptacle 316 and is in electrical contact with the corresponding ground circuit assembly 328. When the ground electrode assembly 208 is removed from the installed position, the bottom electrode surface is consequently moved out of electrical contact with the ground circuit assembly 328. As will become evident from further description below, this breaking of the electrical contact between the bottom electrode surface and the ground circuit assembly 328 is done in a non-destructive manner. That is, reinstalling the ground electrode assembly 208 in the mounting receptacle 316 is all that is required to reestablish electrical contact between the bottom electrode surface and the ground circuit assembly 328. No additional steps such as soldering or coupling components together are required.

Generally, the ground circuit assembly 328 may have any configuration suitable for providing signal communication between the ground electrode 222 and additional circuitry (e.g., measurement electronics 162, FIG. 1), for enabling non-destructive breaking of electrical contact when uninstalling the ground electrode assembly 208, and for facilitating (re-)establishment of electrical contact when (re-)

installing the ground electrode assembly 208. One or more components of the ground circuit assembly 328 may extend upward into the mounting receptacle 316 from the bottom side of the plenum base 204 to facilitate electrical connection with the bottom electrode surface of the ground electrode 222. As a non-limiting example and as illustrated in FIG. 3A, each ground circuit assembly 328 includes an electrically conductive spring 306 and an electrically conductive bottom plug 310. The spring 306 may be located in the mounting receptacle 316. When the ground electrode assembly 208 is installed in the mounting receptacle 316, the bottom electrode surface comes into contact with the spring 306. The bottom plug 310 may be secured to the plenum base 204 from the bottom side (FIG. 3B) and may at least partially extend into the mounting receptacle 316 and into contact with the spring 306.

Continuing with this example and as illustrated in FIG. 3B, plenum base assembly 202 may provide a common ground plane, such as an electrically conductive ground hub 326, shared by (in signal communication with) each ground circuit assembly 328. For this purpose, the ground hub 326 may include any suitable configuration of electrically conductive components for providing signal communication between the ground electrode 222 and additional circuitry (e.g., measurement electronics 162, FIG. 1). As one non-limiting example, the ground hub 326 may be a printed circuit board assembly (PCBA). Also in this example, to complete the circuit between the ground hub 326 and each ground electrode assembly 208, each ground circuit assembly 328 further includes an electrically conductive lug 330 attached to the bottom plug 310, and an electrically conductive wire 332 interconnecting the lug 330 and the ground hub 326. As illustrated, the location of the ground hub 326 may be offset from each mounting receptacle 316 to facilitate making electrical connections with multiple ground electrode assemblies 208 installed in the plenum base 204.

Generally, the various components of the ground circuit assemblies 328 may be composed of any suitable electrically conductive material. In some embodiments, the spring 306 may include a conductive core that is coated with a different conductive material. As one non-limiting example, the spring 306 may include a phosphor bronze core coated with silver. In some embodiments, the bottom plug 310 may include a conductive core that is coated with a different conductive material. As one non-limiting example, the bottom plug 310 may include a brass core coated with silver.

Figure 4A:
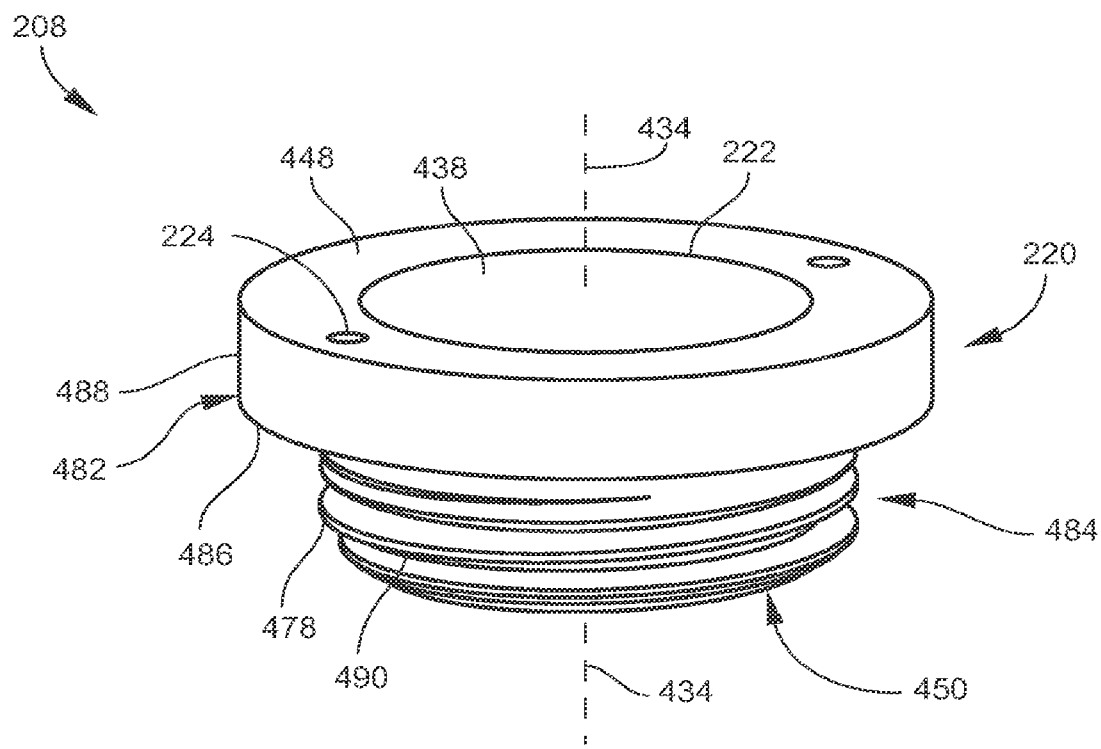
FIG. 4A is a perspective view of a ground electrode assembly according to some embodiments.
Figure 4B:
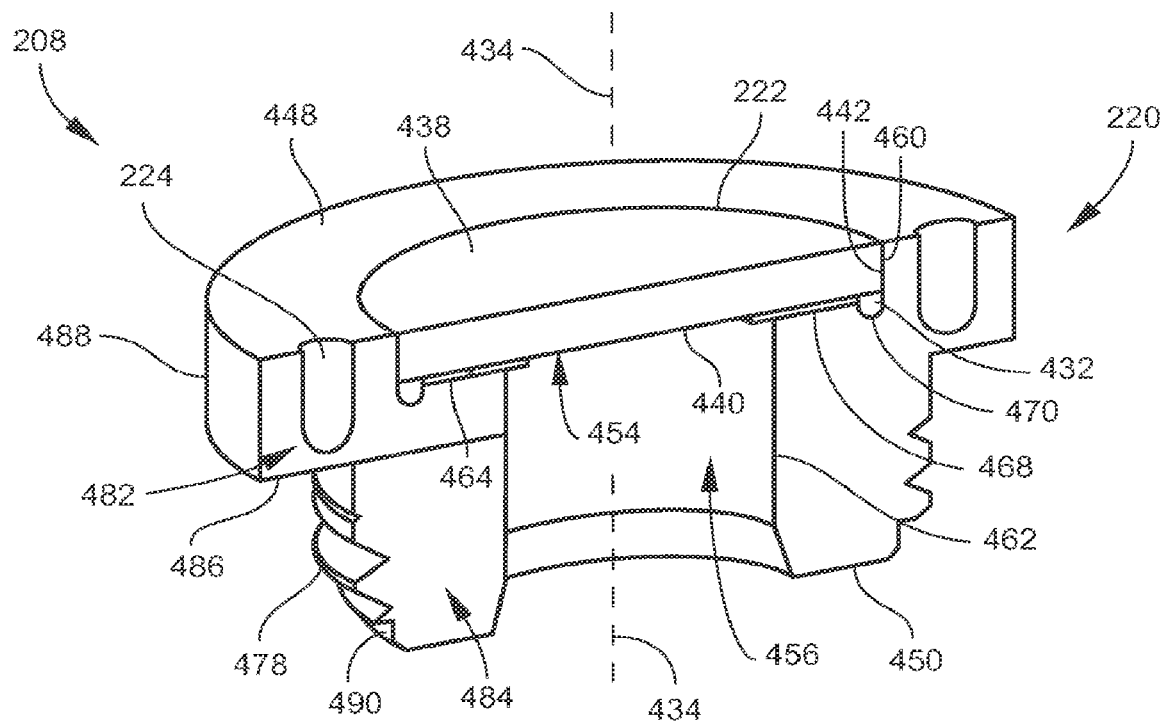
FIG. 4B is a cross-sectional perspective view of the ground electrode assembly.

FIG. 4A is a perspective view of the ground electrode assembly 208 according to some embodiments. FIG. 4B is a cross-sectional perspective view of the ground electrode assembly 208. The ground electrode assembly 208 includes the electrode housing 220, the ground electrode 222 secured in the electrode housing 220, and a sealing member 432 (FIG. 4B) For descriptive purposes, the electrode housing 220 may be considered as having a length or height along an assembly axis 434 and the ground electrode 222 may be considered as having a thickness along the assembly axis 434.

The ground electrode 222 may generally include a top electrode surface 438 (or first outside transverse electrode surface), a bottom electrode surface 440 (or second outside transverse electrode surface) opposing the top electrode surface 438, and an outside lateral electrode surface 442 adjoining the top electrode surface 438 and bottom electrode surface 440. The top electrode surface 438 and bottom electrode surface 440 may be generally transverse to the assembly axis 434, and the outside lateral electrode surface 442 may be generally parallel to the assembly axis 434. In typical embodiments, the ground electrode 222 is a sintered mixture of silver and silver chloride. The ground electrode 222 may generally have any geometry. In the illustrated embodiment, the ground electrode 222 is cylindrical or disk-shaped with a circular cross-section (relative to the assembly axis 434). In other embodiments, the ground electrode 222 may have another type of rounded cross-section (e.g., elliptical), or may be prismatic with a polygonal cross-section. In typical embodiments, the transverse dimension of the ground electrode 222 is greater than its thickness. In the present context, the "transverse dimension" is the dimension characterizing the size of the ground electrode 222 in the plane transverse to the assembly axis 434, and depends on its geometry. Thus, in the case of a circular cross-section (as illustrated) the transverse dimension is the outside diameter, while in the case of polygonal cross-sections the transverse dimension is the distance between opposing sides or corners.

The electrode housing 220 may be composed of any electrically insulating material that is substantially impervious to liquid flow and is sufficiently robust to serve as a permanent support and containment structure for the ground electrode 222. Examples of suitable materials for the electrode housing 220 include, but are not limited to, polycarbonate, polyamides, polyethylene, polyoxymethylene, polystyrene, and polyolefin.

The electrode housing 220 may generally include a top housing surface 448 (or first outside transverse surface), a bottom housing surface 450 (or second outside transverse surface) opposing the top housing surface 448, and an outside lateral housing surface adjoining the top housing surface 448 and bottom housing surface 450. The top housing surface 448 and bottom housing surface 450 may be generally transverse to the assembly axis 434. The outside lateral housing surface may include portions transverse or parallel to the assembly axis 434. The electrode housing 220 may also generally include a first (or upper) chamber 454 that is open at the top housing surface 448, and a second (or lower) chamber 456 that is open at the bottom housing surface 450. The first chamber 454 openly communicates with the second chamber 456 at an internal opening. The first chamber 454 provides a space for receiving the ground electrode 222. The second chamber 456 may provide a space for accommodating one or more components of the ground circuit assembly 328 (FIG. 3B) with which the ground electrode 222 contacts when installed in the plenum base 204, as described elsewhere herein. The geometry of the first chamber 454 may be complementary to the geometry of the ground electrode 222. In the illustrated embodiment, the first chamber 454 and ground electrode 222 have circular cross-sections, while in other embodiments may have polygonal cross-sections. The second chamber 456 may have a circular or polygonal cross-section. In some embodiments, the first chamber 454 and second chamber 456 are both centered on the assembly axis 434.

The first chamber 454 may have a greater transverse dimension than the transverse dimension of the second chamber 456. By this configuration, a portion (e.g., central portion) of the ground electrode 222 is exposed to the second chamber 456 at the internal opening. The first chamber 454 and the ground electrode 222 may be sized such that the top electrode surface 438 is flush or substantially flush with the top housing surface 448.

In another embodiment the top electrode surface 438 is slightly recessed (e.g., by 1 to 3 mm) relative to the top housing surface 448, which allows an agar bridge (conductive gelatin) to be placed between the ground electrode 222 and the internal buffer solution 152. This agar bridge delays the release of contaminants from the ground electrodes 222 into the internal buffer and reduces their concentrations.

Generally, the first chamber 454 and second chamber 456 are defined by one or more inside housing surfaces of the electrode housing 220. In the illustrated embodiment, the electrode housing 220 includes a first inside lateral housing surface 460 adjoining the top housing surface 448 and a second inside lateral housing surface 462 adjoining the bottom housing surface 450. The first inside lateral housing surface 460 and second inside lateral housing surface 462 surround the assembly axis 434 (e.g., coaxial about the axis 434 in circular cross-sectional geometries). The electrode housing 220 also includes an inside shoulder 464 between the first inside lateral housing surface 460 and second inside lateral housing surface 462. The first inside lateral housing surface 460 and second inside lateral housing surface 462 may be generally parallel to the assembly axis 434, and the shoulder 464 may be generally transverse to the assembly axis 434. The inside shoulder 464 may adjoin the first inside lateral housing surface 460 and the second inside lateral housing surface 462. The first inside lateral housing surface 460 and the inside shoulder 464 define the first chamber 454, the inside shoulder 464 defines the internal opening, and the second inside lateral housing surface 462 defines the second chamber 456.

The ground electrode 222 may be secured to the electrode housing 220 by any suitable means. The ground electrode 222 may be secured in a manner that minimizes fluid leakage from the top housing surface 448 (which, in use, is part of the plenum chamber containing internal buffer solution as described above), through the first chamber 454, and into the second chamber 456. For this purpose, the transverse dimension of the ground electrode 222 may be slightly greater than the transverse dimension of the first chamber 454, whereby the ground electrode 222 is securely fixed in the first chamber 454 by press-fitting.

In addition, the sealing member 432 may be configured and located to fluidly isolate the interface from the second chamber 456. In the illustrated embodiment, the sealing member 432 surrounds the assembly axis 434 in a continuous manner, such as a ring or bead. The sealing member 432 may be disposed between the bottom electrode surface 440 and the shoulder 464, without completely sealing the entire bottom electrode surface 440 so as to enable the bottom electrode surface 440 to make electrical contact with a portion of the ground circuit assembly 328 (FIGS. 3A and 3B) located in the second chamber 456. The sealing member 432 may be located at the corner where the first lateral inside housing surface 460 meets the invisible shoulder 464. In some embodiments (as illustrated), the inside shoulder 464 may include a generally flat transverse section 468 adjoining the second lateral inside housing surface 462 at the internal opening, and a channel or groove 470 between the first lateral inside housing surface 460 and the transverse section 468. The channel 470 may surround the assembly axis 434 in a continuous manner, and may have a depth extending below the transverse section 468. The sealing member 432 may be located in the channel 470.

In addition to providing a fluid seal, the sealing member 432 may be configured for securing the ground electrode 222 to the housing 220 by adhesion, bonding, etc. The sealing member 432 may be composed of any material suitable for this purpose. For example, the sealing member 432 may be formed during assembly of the ground electrode assembly 208, by applying an initially fluent sealing material to the channel 470 and pressing the ground electrode 222 into contact with the sealing material, after which time the sealing material hardens by curing, drying, etc. Some excess sealing material may be permitted to creep out from the channel 470 and remain between the bottom electrode surface 440 and the transverse section 468 of the inside shoulder 464, while a portion of the bottom electrode surface 440 remains exposed to the second chamber 456 to enable the electrical connection with ground circuit assembly 328 (FIG. 3B) as described above. Examples of suitable sealing materials include, but are not limited to, epoxy, rubber, silicone, and felt. In some embodiments, a structural barrier (not shown) optionally may be provided between the channel 470 and the internal opening to limit the creeping of the sealing material. The structural barrier may surround the assembly axis 434 in a continuous manner, such as a ring.

Figure 6:
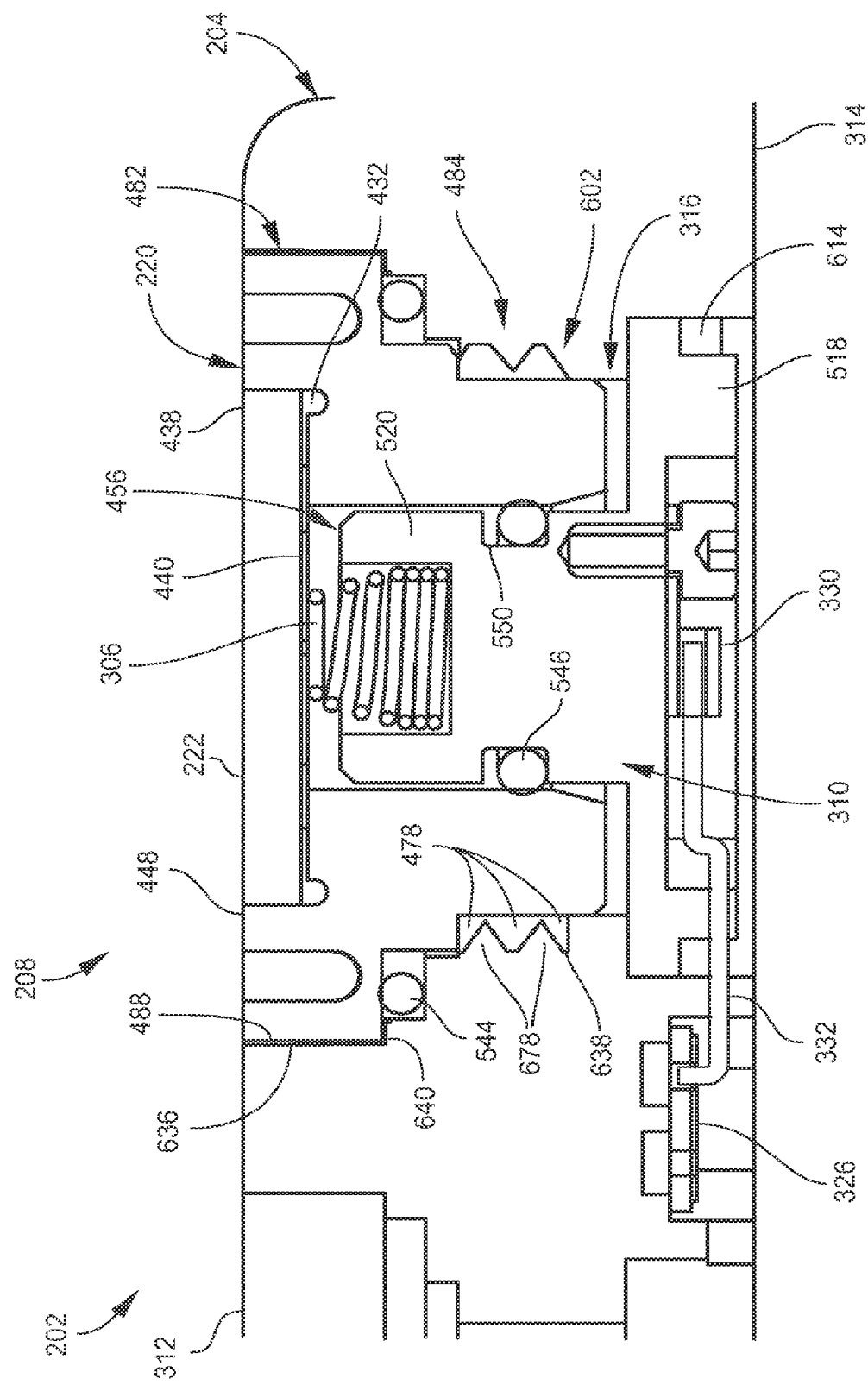
FIG. 6 is a cross-sectional side elevation view of a section of the plenum base assembly according to some embodiments, illustrating the ground electrode assembly installed in the mounting receptacle.

The electrode housing 220 may further include an engaging device or component 478 configured for removably engaging the electrode housing 220 with the plenum base 204 (FIGS. 3A and 3B). In this case, installing the ground electrode assembly 208 may include engaging the electrode housing 220 with the plenum base 204, and uninstalling the ground electrode assembly 208 may include disengaging the electrode housing 220 from the plenum base 204. In some embodiments, the engaging device 478 may be a first engaging device configured for removably engaging a second engaging device or component 678 of the plenum base 204 (FIG. 6). As one non-limiting example, the first engaging device 478 may be or include a first threaded section of the electrode housing 220 and the second engaging device 678 may be or include a second threaded section of the plenum base 204. That is, the first engaging device 478 and second engaging device 678 may include complementary thread configured for mating with each other. In the illustrated embodiment, the first threaded section may be located on or integrated with (i.e., a part of, or integrally formed with) an outside surface of the electrode housing 220, and the second threaded section may be located on or integrated with an inside surface of each mounting receptacle 316 of the plenum base 204. Hence, the first threaded section may include a male thread and second threaded section may include a female thread. In this embodiment, the ground electrode assembly 208 is installed by rotating (e.g., screwing) it into the mounting receptacle 316 in one direction, and is uninstalled by rotating (e.g., unscrewing) it out from the mounting receptacle 316 in the opposite direction. As noted above, the electrode housing 220 may include a tool engagement component 224 configured for engaging a tool manipulated by a user to aid in installing and uninstalling the ground electrode assembly 208.

In some embodiments, the electrode housing 220 may include an upper section or flange section 482 and a lower section 484. The upper section 482 surrounds the first chamber 454, and may additionally surround a portion of the second chamber 456. The lower section 484 surrounds at least a portion of the second chamber 456. The flange section 482 may have a greater outside transverse dimension (e.g., diameter) than that of the lower section 484. The flange section 482 may be bounded by the top housing surface 448, a bottom flange surface 486, and a first outside lateral housing surface 488 adjoining the top housing surface 448 and the bottom flange surface 486. The lower section 484 may be bounded by the bottom flange surface 486, the bottom housing surface 450 and a second outside lateral housing surface 490, which may be adjoined to the bottom flange surface 450. As illustrated, the first engaging device 478 may be located on or integrated with the second outside lateral housing surface 490.

Figure 5:
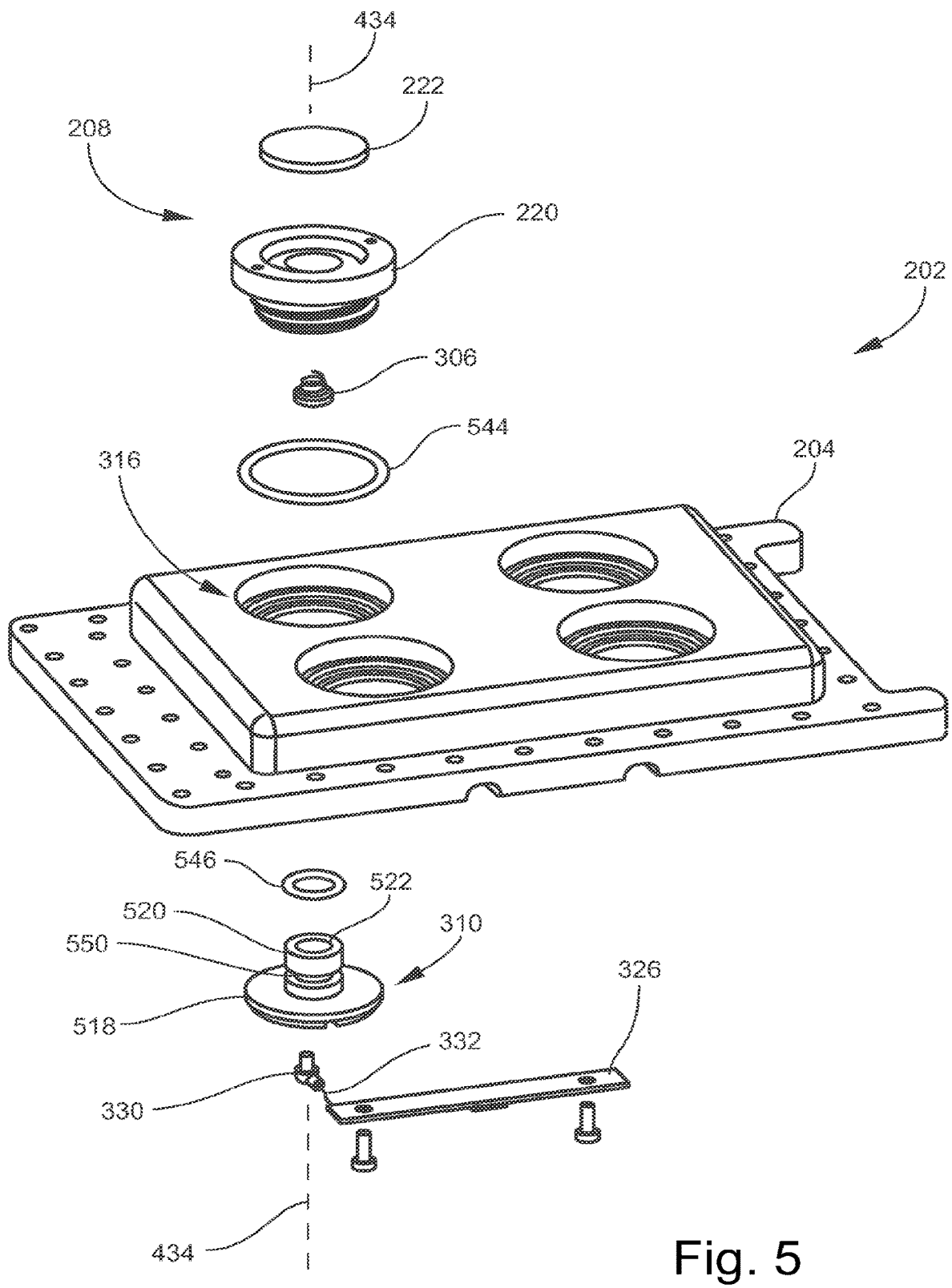
FIG. 5 is a perspective view of the plenum base assembly according to some embodiments.

FIG. 5 is a perspective view of the plenum base assembly 202 according to some embodiments. FIG. 5 also includes an exploded view of components of one of the ground electrode assemblies 208 and corresponding ground circuit assembly 328, along an assembly axis 434 passing through one of the mounting receptacles 316 of the plenum base 204, according to some embodiments. FIG. 6 is a cross-sectional side elevation view of a section of the plenum base assembly 202 according to some embodiments, illustrating the ground electrode assembly 208 installed in the mounting receptacle 316. Each mounting receptacle 316 is generally defined by an inside receptacle surface extending from the top base surface 312 to or toward the bottom base surface 314 and surrounding the assembly axis 434. The mounting receptacle 316 may be configured such that the ground electrode assembly 208 (the top electrode surface 438 and/or top housing surface 448) when installed is flush or substantially flush with the top base surface 312, although in some embodiments the top electrode surface 438 may be recessed as described above. FIG. 6 schematically illustrates an engagement interface 602 between the ground electrode assembly 208 and the inside receptacle surface, formed by engaging the first engaging device 478 with the second engaging device 678. As described above, in some embodiments the engagement interface 602 may be a thread interface formed by mating an external thread located on or part of the outside surface of the electrode housing 220 with an internal thread located on or part of the inside receptacle surface.

As described above, one or more components of the ground circuitry may extend upward into the second chamber 456 of the electrode housing 220 to facilitate electrical connection with the bottom electrode surface 440. In the illustrated embodiment, the spring 306 of the ground circuitry is located in the second chamber 456. When the ground electrode assembly 208 is installed in the mounting receptacle 316, the bottom electrode surface 440 comes into contact with the spring 306. During installation, as the ground electrode assembly 208 moves further into the mounting receptacle 316 (such as by rotating or screwing, as described above), the spring 306 is compressed and thus imparts a biasing force against the bottom electrode surface 440, thereby forming a reliable, low-resistance electrical contact between the spring 306 and the bottom electrode surface 440. In embodiments where the bottom electrode surface 440 is composed of a relatively soft material such as silver, the movement of the ground electrode assembly 208 during installation may cause the end of the spring 306 to "bite" into the silver, thereby further improving the electrical connection. In some embodiments in which the engagement interface 602 between the electrode housing 220 and the inside receptacle surface is formed by the mating of internal and external threads, the helical winding of the spring 306 may turn in an opposite handedness (or opposite sense) than the helices of the threads. For example, the spring 306 may be wound clockwise while the threads are wound counterclockwise. In such a case, the ground electrode assembly 208 is screwed in the opposite direction to the winding of the spring 306, which may improve the "biting" contact between the spring 306 and the bottom electrode surface 440.

The bottom plug 310 of the ground circuitry may be secured to the plenum base 204 by any suitable means such as, for example, a potting material 614 such as epoxy. The bottom plug 310 may include a base portion 518 configured to provide a lower boundary of the mounting receptacle 316, and a central portion 520 that extends upward from the base portion 518 into the second chamber 456 of the electrode housing 220 and into contact with the spring 306. By this configuration, when the ground electrode assembly 208 is installed in the mounting receptacle 316, the spring 306 is compressed between the bottom electrode surface 440 and the bottom plug 310, thereby forming a good electrical contact with the bottom plug 310 as well as the bottom electrode surface 440. In some embodiments, the bottom plug 310 may include a recess or seat 522 into which a portion of the spring 306 is located.

In some embodiments, the inside receptacle surface includes a first inside lateral receptacle surface 636 adjoining the top base surface 312 and a second inside lateral receptacle surface 638, both surrounding the assembly axis 434 (e.g., coaxial about the axis 434 in circular cross-sectional geometries) and generally parallel to the assembly axis 434. The engagement interface 602 between the ground electrode assembly 208 and the mounting receptacle 316 (e.g., threaded engagement) may be located at the second inside lateral receptacle surface 638. The inside receptacle surface may also include a generally transversely oriented shoulder 640 between the first inside lateral receptacle surface 636 and second inside lateral receptacle surface 638. In embodiments where the electrode housing 220 includes the flange section 482, the shoulder 640 may serve as a stop that limits further movement of the ground electrode assembly 208 into the mounting receptacle 316. That is, at the fully installed position, the bottom flange surface 486 may contact the shoulder 640.

The top base surface 312, top housing surface(s) 448, and top electrode surface(s) 438 may define the lower boundary of the plenum reservoir, which in use contains internal buffer solution as described above. The ground electrode assembly 208 may be mounted in the mounting receptacle 316 in a manner that avoids fluid leakage from the plenum reservoir 140 into the open spaces of the interior of the mounting receptacle 316 and thereby prevents wetting of the electrically conductive components. Also desirable is to avoid collecting air in gaps between the ground electrode assembly 208 and the mounting receptacle 316. For these purposes, the transverse dimension of the first inside lateral receptacle surface 636 may be only slightly greater than the transverse dimension of the electrode housing 220 (i.e., the first outside lateral housing surface 488), thereby minimizing the upper gap between the electrode housing 220 and the first inside lateral housing surface 636.

In addition, one or more sealing members such as O-rings, gaskets, or the like may be configured and located to fluidly isolate the plenum reservoir 140 from the mounting receptacle 316. In the illustrated embodiment, a first sealing member 544 is located between the first outside lateral housing surface 488 and engagement interface 602, e.g., in a space between the flange section 482 and lower section 484 of the electrode housing 220. A second sealing member 546 is located in the gap between the bottom plug 310 and an inside surface defining the second chamber 456 of the electrode housing 220. The bottom plug 310 may include a groove or channel 550 in which the second sealing member 546 is located. Hence, the illustrated embodiment, to reach the interior of the mounting receptacle 316 liquid would need to pass through the first sealing member 544, the engagement interface 602, and the second sealing member 546.

Figure 7A:
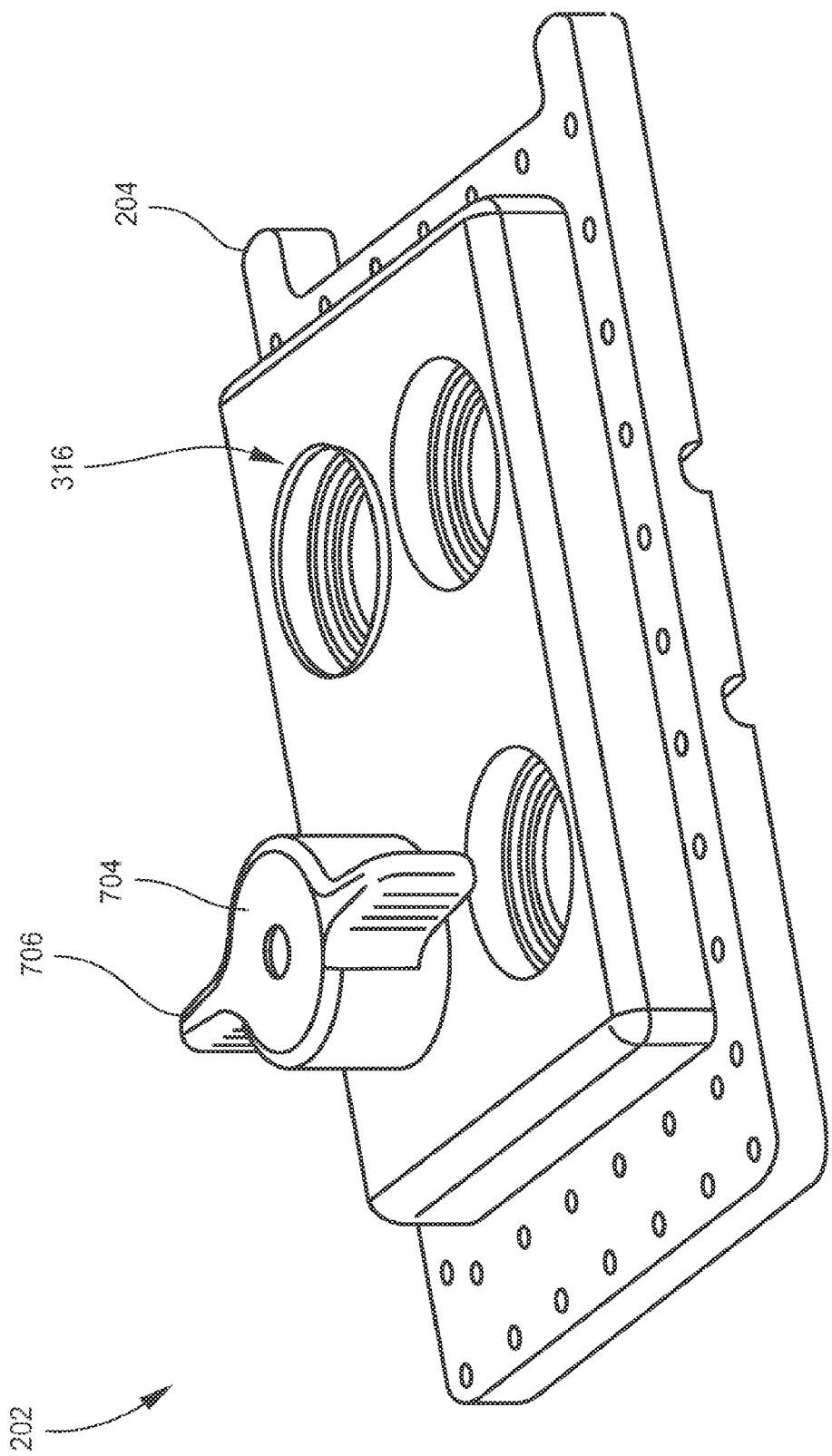
FIG. 7A is a perspective view of the plenum base assembly similar to FIG. 3A, illustrating a tool engaging the ground electrode assembly according to some embodiments.
Figure 7B:
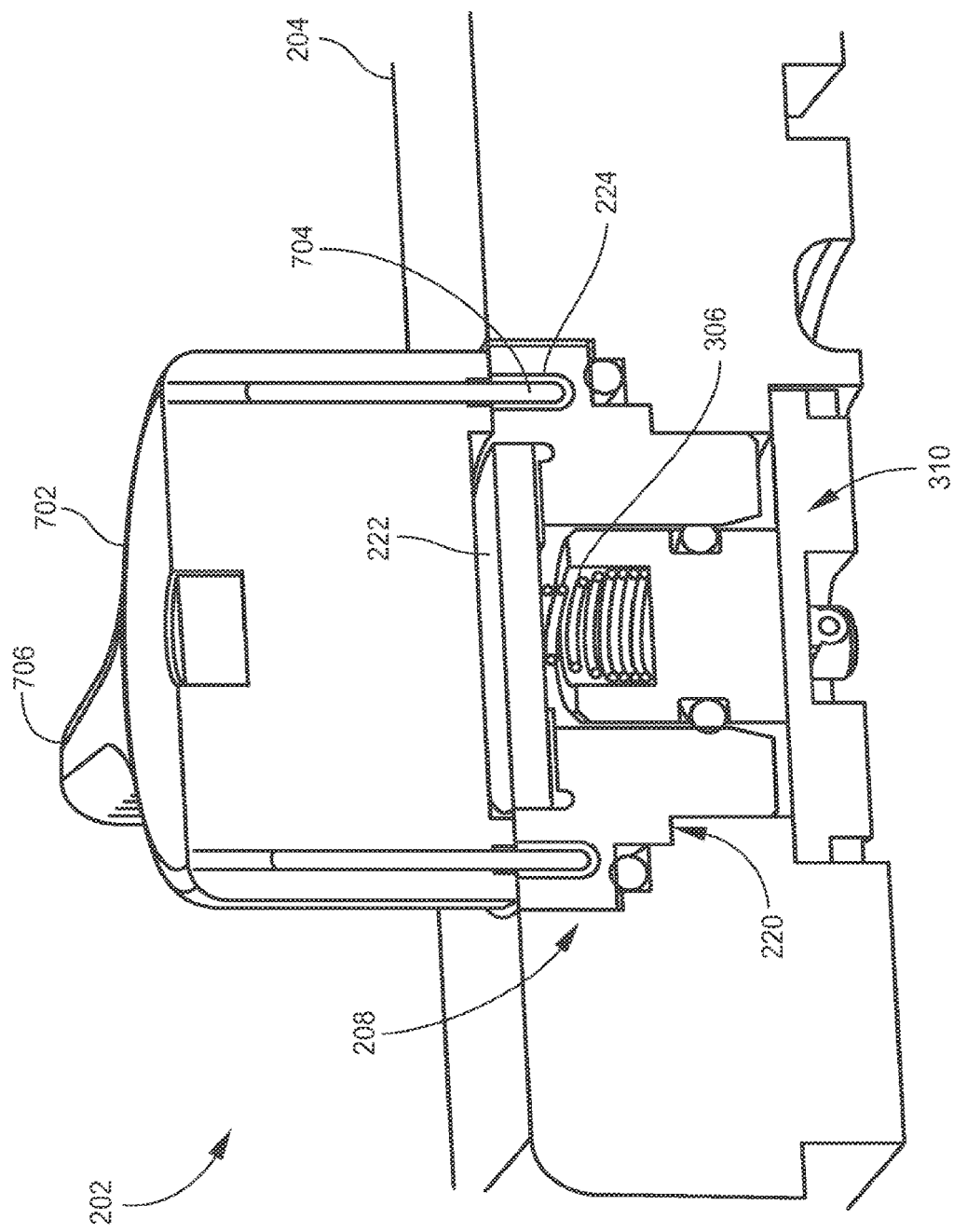
FIG. 7B is a cross-sectional perspective view of a section of the plenum base assembly illustrated in FIG. 7A.

FIG. 7A is a perspective view of the plenum base assembly 202 similar to FIG. 3A, illustrating a tool 702 engaging the ground electrode assembly 208 according to some embodiments. FIG. 7B is a cross-sectional perspective view of a section of the plenum base assembly 202 illustrated in FIG. 7A. The tool 702 is configured for engaging the ground electrode assembly 208 in a manner facilitating removal and subsequent reinstallation of the ground electrode assembly 208, such as by rotating (e.g., unscrewing) the ground electrode assembly 208 out from the plenum base 204 and subsequently rotating (e.g., screwing) the ground electrode assembly 208 back into the plenum base 204 after rejuvenation as described by example elsewhere herein. In the illustrated embodiment, for this purpose the tool 702 includes one or more engagement members such as prongs 704 that are inserted into sockets or receptacles 224 of the ground electrode assembly 208. The tool 702 may also include a component configured for facilitating handling and manipulation of the tool 702 by the user, such as one or more handles or wings 706. The tool 702 may include other features for improving grip such as knurling, ribs, etc.

As noted above, with continued use of the ground electrodes 222 in conjunction with electrophysiological assays, contaminants and/or toxins build up in the bulk of the ground electrodes 222 resulting in impaired performance. In embodiments disclosed herein, the ground electrode assemblies 208 are individually removable and re-installable with significant ease and in a non-destructive manner, and without the need for undertaking time-consuming steps for re-establishing electrical connections. Consequently, the ground electrodes 222 are easily rejuvenated (or cleaned) with minimal downtime to the electrophysiological apparatus in which the ground electrodes 222 operate. A contaminated ground electrode assembly 208 (i.e., a ground electrode assembly 208 containing a contaminated ground electrode 222) need only be uninstalled in the manner described above and subjected to rejuvenation (or cleaning), while a fresh ground electrode assembly is installed in the plenum base 204 in the place of the contaminated ground electrode assembly 208, thus enabling the plenum assembly 200 to continue to be operated with minimal downtime. After a contaminated ground electrode assembly 208 has been rejuvenated, the rejuvenated ground electrode assembly 208 may be reinstalled in the plenum base 204 in the place of an existing ground electrode assembly. The existing ground electrode assembly being replaced may at this time be contaminated, and thus may be subjected to the rejuvenation process.

In some embodiments, a ground electrode assembly 208 may be rejuvenated by uninstalling it as described above, and immersing it in a bath containing a rejuvenating (or cleaning) agent or fluid. Examples of rejuvenating agents include, but are not limited to, potassium chloride solutions, ethylenediaminetetraacetic acid solutions, and citric acid solutions. Once the ground electrode assembly 208 has been immersed in the bath, the rejuvenating agent may diffuse into the bulk of the ground electrode 222. Because the ground electrode 222 is mounted in the individually removable electrode housing 220 in a manner such that neither the top electrode surface 438 nor most of the bottom electrode surface 440 is hermetically sealed, both the top electrode surface 438 and the bottom electrode surface 440 are exposed to the rejuvenating agent after immersion. Consequently, the rejuvenating agent is able to diffuse into the bulk of the ground electrode 222 from both the top electrode surface 438 and the bottom electrode surface 440. This results in a more effective rejuvenating of (purging of contaminants and/or toxins from) the ground electrode 222, and complete rejuvenation occurs over a much shorter time compared to conventional ground electrodes. As noted above, conventional ground electrodes are not individually removable from the plenum base, and only their top electrode surfaces are exposed to the rejuvenating agent.

In other embodiments, a ground electrode assembly 208 may be rejuvenated by uninstalling it as described above, placing it in a rejuvenating vessel (or cleaning vessel), and applying a pressure differential across the thickness of the ground electrode 222. The applied pressure differential is effective to actively perfuse the rejuvenating agent through the thickness of the ground electrode 222, which may enhance (increase) the effectiveness of the rejuvenation process and shorten the time required for completing the rejuvenation process even further. The applied pressure differential required may be relatively small, for example, 5 to 10 psi. The applied pressure differential may be realized by applying either positive pressure or negative pressure (vacuum) to the ground electrode 222.

Figure 8B:
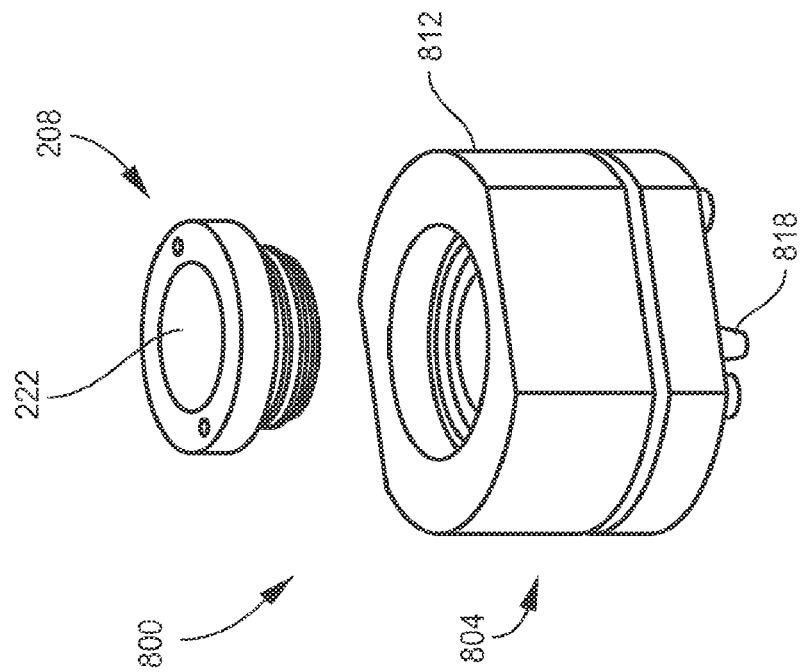
FIG. 8B is a perspective view of the rejuvenating apparatus and the ground electrode assembly, prior to mounting the ground electrode assembly to the rejuvenating apparatus or after removing the ground electrode assembly from the rejuvenating apparatus.
Figure 8A:
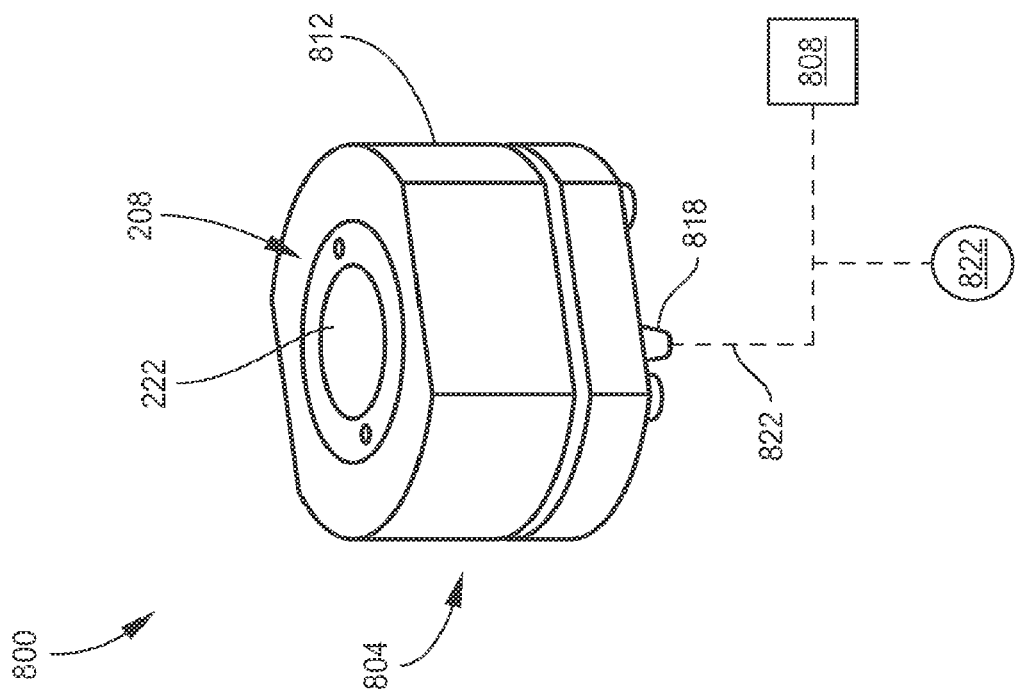
FIG. 8A is a perspective view of an example of a rejuvenating apparatus (or cleaning apparatus) to which a ground electrode assembly has been mounted according to some embodiments.
Figure 8C:
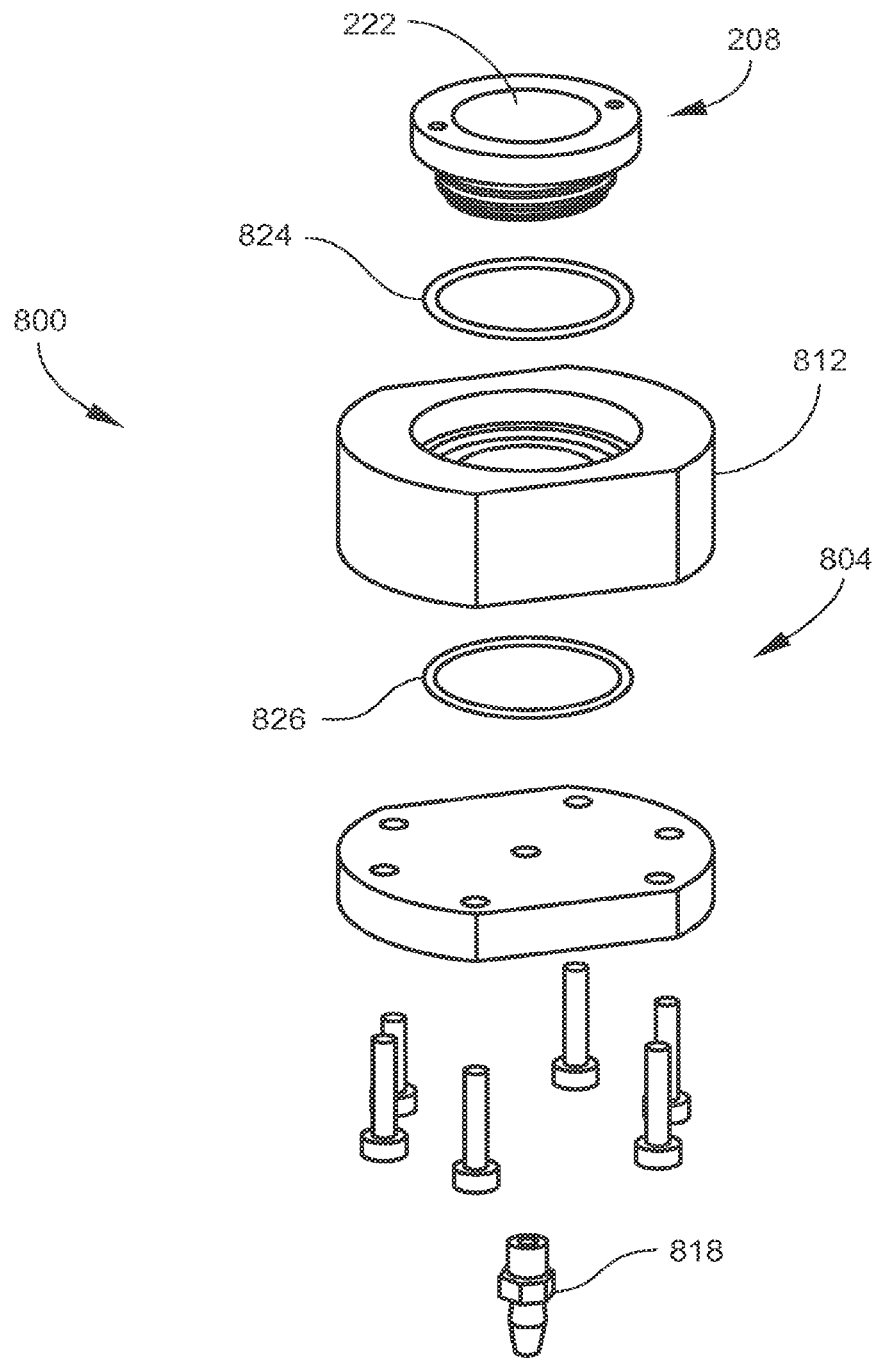
FIG. 8C is an exploded perspective view of the rejuvenating apparatus in disassembled form, along with the ground electrode assembly.
Figure 8D:
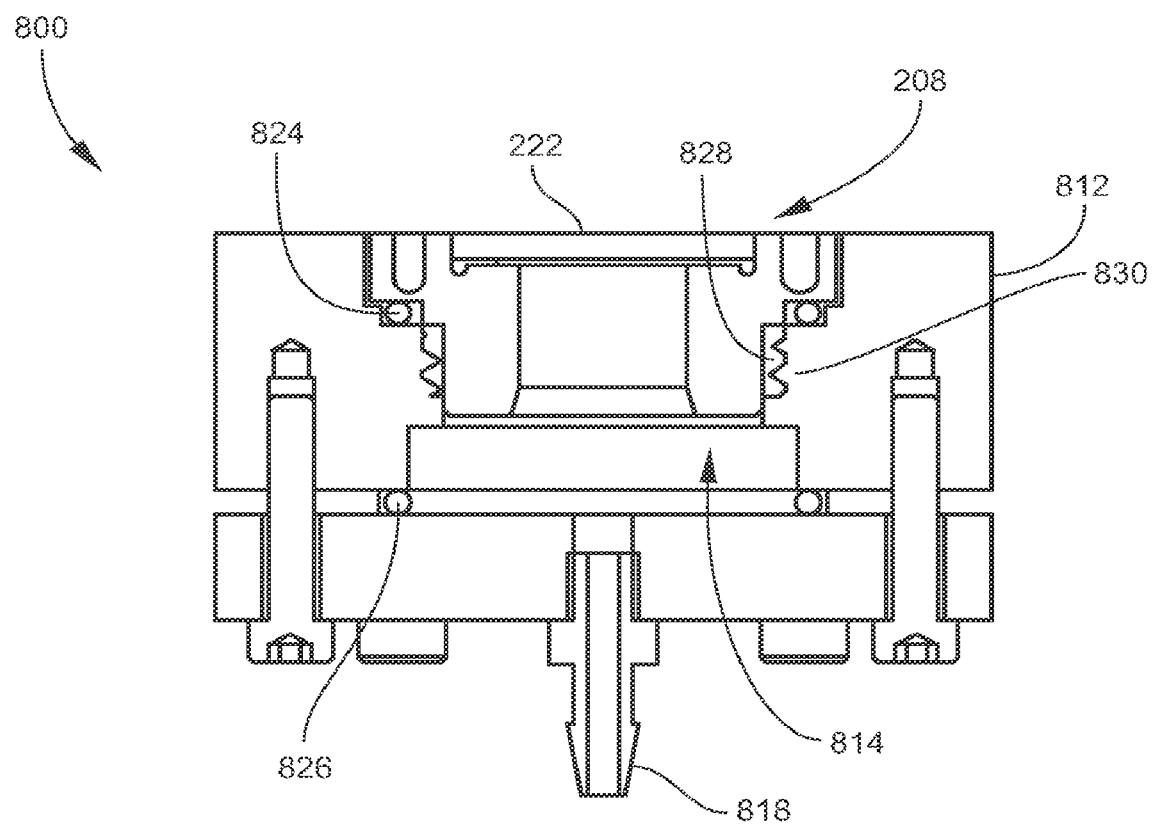
FIG. 8D is a cross-sectional elevation view of the rejuvenating apparatus with the ground electrode assembly attached thereto.

FIG. 8A is a perspective view of an example of a rejuvenating apparatus (or cleaning apparatus) 800 to which a ground electrode assembly 208 has been mounted according to some embodiments. FIG. 8B is a perspective view of the rejuvenating apparatus 800 and the ground electrode assembly 208, prior to mounting the ground electrode assembly 208 to the rejuvenating apparatus 800 or after removing the ground electrode assembly 208 from the rejuvenating apparatus 800. FIG. 8C is an exploded perspective view of the rejuvenating apparatus 800 in disassembled form, along with the ground electrode assembly 208. FIG. 8D is a cross-sectional elevation view of the rejuvenating apparatus 800 with the ground electrode assembly 208 attached thereto.

The rejuvenating apparatus 800 may include a vessel 804 communicating with a positive pressure-applying device 808 (FIG. 8A). The vessel 804 may include a vessel body 812 defining an interior chamber 814. The ground electrode assembly 208 is attachable to the vessel body 812 so as to close the interior chamber 814 in a fluid-tight manner. The vessel 804 may include a fluid port or fitting 818 coupled to the vessel body 812 so as to communicate with the interior chamber 814, thus serving as an input port. The fluid port 818 may be configured to be coupled directly to the positive pressure-applying device 808 or to tubing 822 (FIG. 8A) between the fluid port 818 and the positive pressure-applying device 808. The positive pressure-applying device 808 may have any suitable configuration for applying positive pressure to the interior chamber 814. As one non-limiting example, the positive pressure-applying device 808 may be a positive displacement device such as a syringe. Alternatively, the positive pressure-applying device 808 may be another type of pump.

The ground electrode assembly 208 is attachable to the vessel body 812 so as to close the interior chamber 814 in a fluid-tight manner. The rejuvenating apparatus 800 may include one or more sealing members 824 and 826 such as, for example, O-rings (FIG. 8A) for this purpose. The tool 702 described above may be utilized to facilitate installing and removing the ground electrode assembly 208 in a manner analogous to that described above. In some embodiments, the interior chamber may be configured similarly to the inside surface of the mounting receptacles 316 of the plenum base 204 (see, e.g., FIGS. 5 and 6). In this case, the ground electrode assembly 208 may be installed in the vessel 804 in a manner similar to installation in the mounting receptacle 316, for example by mating a thread 828 of the ground electrode assembly 208 with a thread 830 of the vessel body 812 (FIG. 8D). The ground electrode assembly 208 may be installed such that the bottom electrode surface 440 faces toward the interior chamber 814 while the top electrode surface 438 faces away from the interior chamber 814. After installing the ground electrode assembly 208, the positive pressure-applying device 808 is operated to generate a pressure differential across the ground electrode 222, thereby inducing perfusion of rejuvenating fluid through the ground electrode 222. A pressure gauge 822 may be coupled to the rejuvenating apparatus 800 to enable the applied pressure to be monitored during the rejuvenating operation.

FIGS. 8A to 8D depict the vessel body 812 as including two parts coupled together by fasteners. This, however, is but one possible embodiment. In other embodiments, the vessel body 812 may have a unitary (single-piece) configuration, in which case fasteners are not needed and which may eliminate the need for the lower sealing member 826 shown in FIGS. 8C and 8D.

In some embodiments, the rejuvenating apparatus 800 may additionally include an output port or fitting (not shown) coupled to a waste receptacle that collects spent rejuvenating fluid. By this configuration, the pump may be operated to continuously flow fresh rejuvenating fluid from a supply reservoir through the vessel 804 during part of all of the rejuvenating process.

Figure 9:
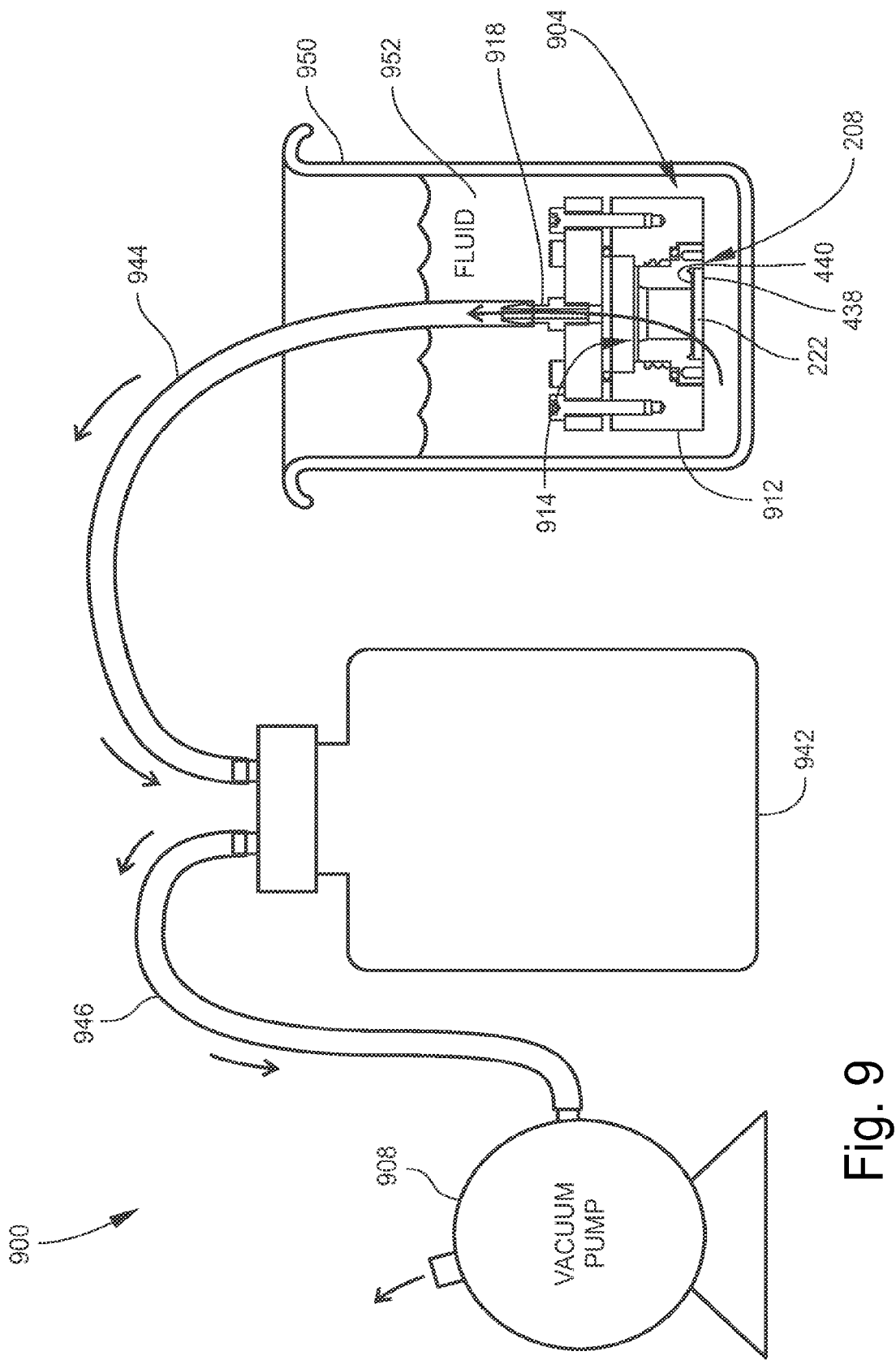
FIG. 9 is a schematic view of an example of a rejuvenating apparatus (or cleaning apparatus) in which a ground electrode assembly has been placed according to other embodiments.

FIG. 9 is a schematic view of an example of a rejuvenating apparatus (or cleaning apparatus) 900 in which a ground electrode assembly 208 has been placed according to other embodiments. The rejuvenating apparatus 900 may include a vessel 904 communicating with a negative pressure-applying device such as a vacuum pump 908. The vessel 904 may include a vessel body 912 defining an interior chamber 914. The vessel 904 may include a fluid port or fitting 918 that serves as an output port and communicates with the vacuum pump 908 via an output line. In some embodiments, the interior chamber 914 may be configured similarly to the inside surface of the mounting receptacles 316 of the plenum base 204, as described above in conjunction with FIG. 8. The rejuvenating apparatus 900 may additionally include a liquid trap 942 between the fluid port 918 and the vacuum pump 908 to prevent liquid from entering the vacuum pump 908. In this case, the output line may include tubing 944 between the fluid port 918 and the liquid trap 942, and tubing 946 between the liquid trap 942 and the vacuum pump 908. The rejuvenating apparatus 900 may further include a supply reservoir 950 containing rejuvenating fluid 952.

In operation, the ground electrode assembly 208 is placed in or mounted to the vessel 904, and the vessel 904 with the ground electrode assembly 208 is immersed in the reservoir 950 such that the top electrode surface 438 is exposed directly to the rejuvenating fluid 952. The vacuum pump 908 is then operated to generate a pressure differential across the ground electrode 222, thereby inducing perfusion of rejuvenating fluid 932 through the ground electrode 222 predominantly in a direction from the top electrode surface 438 to the bottom electrode surface 440.

In some embodiments, the vessel 804 or 904 may be sized to accommodate a plurality of ground electrode assemblies 208 simultaneously. Alternatively, the rejuvenating apparatus 800 or 900 may include a plurality of vessels 804 or 904 for containing respective ground electrode assemblies 208. One or more input ports and/or output ports may be provided in these embodiments.

It will be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for rejuvenating a ground electrode assembly, the method comprising:
   removing the ground electrode assembly from a mounted position in a plenum base, wherein the ground electrode assembly comprises a housing and a porous electrode positioned in the housing, and at the mounted position the ground electrode assembly is in a mounting receptacle of the plenum base and the electrode is in electrical contact with a ground circuit in the mounting receptacle, and wherein removing the ground electrode assembly comprises moving the electrode out of electrical contact with the ground circuit in a non-destructive manner;
   threadably mating the ground electrode assembly with a vessel body defining an interior chamber, wherein the electrode is disposed proximate an outer surface of the vessel body and distal the interior chamber, and wherein the vessel body comprises a fluid port disposed opposite the electrode;
   connecting the fluid port to a pressure-applying device;
   immersing the ground electrode assembly in a rejuvenating fluid for a period of time; and
   activating the pressure-applying device to perfuse the rejuvenating fluid through the electrode.

2. The method of claim 1, comprising, after immersing, mounting the ground electrode assembly in the mounting receptacle such that the electrode makes electrical contact with the ground circuit.

3. The method of claim 1, wherein the electrode comprises a top electrode surface, a bottom electrode surface, and an electrode thickness between the top electrode surface and the bottom electrode surface.

4. The method of claim 1, wherein the electrode comprises a top electrode surface, a bottom electrode surface, and an electrode thickness between the top electrode surface and the bottom electrode surface, and wherein activating the pressure-applying device comprises applying a pressure differential across the electrode thickness to perfuse the rejuvenating fluid through the electrode thickness.

5. The method of claim 4, wherein the electrode is positioned in the housing such that immersing the ground electrode assembly exposes at least a portion of the top electrode surface and at least a portion of the bottom electrode surface to the rejuvenating fluid.

\* \* \* \* \*